United States Patent
Natsume et al.

(10) Patent No.: US 9,849,587 B2
(45) Date of Patent: Dec. 26, 2017

(54) OPERATION COMMAND GENERATION DEVICE, OPERATION COMMAND GENERATION METHOD, NON-TRANSITORY COMPUTER-READABLE STORAGE MEDIUM, AND PROCESS SYSTEM

(71) Applicants: NATIONAL INSTITUTE OF ADVANCED INDUSTRIAL SCIENCE AND TECHNOLOGY, Tokyo (JP); Kabushiki Kaisha Yaskawa Denki, Kitakyushu-shi, Fukuoka (JP); Robotic Biology Institute Inc., Tokyo (JP)

(72) Inventors: Toru Natsume, Zushi (JP); Takashi Nagasaki, Kitakyushu (JP); Makoto Umeno, Kitakyushu (JP); Tatsuro Ipposhi, Kitakyushu (JP); Hirokazu Kariyazaki, Kitakyushu (JP)

(73) Assignees: NATIONAL INSTITUTE OF ADVANCED INDUSTRIAL SCIENCE AND TECHNOLOGY, Tokyo (JP); KABUSHIKI KAISHA YASKAWA DENKI, Kitakyushu-Shi, Fukuoka (JP); ROBOTIC BIOLOGY INSTITUTE INC., Tokyo (JP)

( * ) Notice: Subject to any disclaimer, the term of this patent is extended or adjusted under 35 U.S.C. 154(b) by 0 days.

(21) Appl. No.: 14/945,437

(22) Filed: Nov. 19, 2015

(65) Prior Publication Data
US 2016/0144506 A1    May 26, 2016

(30) Foreign Application Priority Data
Nov. 21, 2014    (JP) .................................. 2014-237201

(51) Int. Cl.
G06F 7/00 (2006.01)
B25J 9/16 (2006.01)
G01N 35/00 (2006.01)

(52) U.S. Cl.
CPC ............ *B25J 9/1602* (2013.01); *B25J 9/1612* (2013.01); *B25J 9/1656* (2013.01); *B25J 9/1661* (2013.01);
(Continued)

(58) Field of Classification Search
USPC ........................................................ 700/213
See application file for complete search history.

(56) References Cited

U.S. PATENT DOCUMENTS 5,841,959 A * 11/1998 Guiremand ............ B25J 9/1671
                                                            345/440
5,930,461 A    7/1999 Bernstein et al.
(Continued)

FOREIGN PATENT DOCUMENTS

EP    0496785 A1    8/1992
JP    2005-121476 A    5/2005
(Continued)

OTHER PUBLICATIONS

European Search Report dated Apr. 13, 2016 for corresponding EP application No. 15195512.7.
(Continued)

*Primary Examiner* — Kyle Logan
(74) *Attorney, Agent, or Firm* — Hubbs, Enatsky & Inoue PLLC

(57) ABSTRACT

Provided is an operation command generation device including: an execution order determination unit configured to determine, based on respective arrangement positions of a plurality of process symbols each representing a process for a process subject on a protocol chart including the plurality
(Continued)

of process symbols, an execution order of the plurality of process symbols; and a process symbol conversion unit configured to respectively convert the plurality of process symbols into jobs for a process system including at least a robot so that processes represented by the plurality of process symbols are executed in the execution order determined by the execution order determination unit.

21 Claims, 19 Drawing Sheets

(52) U.S. Cl.
CPC .............. *G01N 35/0092* (2013.01); *G05B 2219/36025* (2013.01); *G05B 2219/40113* (2013.01); *G05B 2219/45092* (2013.01); *Y10S 901/02* (2013.01)

(56) References Cited

U.S. PATENT DOCUMENTS

| | | | |
|---|---|---|---|
| 6,594,537 B1 * | 7/2003 | Bernstein | B25J 9/1671 700/100 |
| 2003/0004612 A1 | 1/2003 | Domanico et al. | |
| 2004/0208795 A1 * | 10/2004 | Toi | G01N 35/1011 422/400 |
| 2007/0048863 A1 | 3/2007 | Rodgers et al. | |
| 2010/0202024 A1 | 8/2010 | Carey | |

FOREIGN PATENT DOCUMENTS

| | | |
|---|---|---|
| JP | 2009-502168 A | 1/2009 |
| JP | 2010-127681 A | 6/2010 |
| JP | 2011-033395 A | 2/2011 |
| JP | 2012-117880 A | 6/2012 |

OTHER PUBLICATIONS

European Search Report dated Apr. 7, 2016 for corresponding EP application No. 15195511.9.
PCT/ISA/237 with PCT/IB338 and PCT/IB/373 of Dec. 22, 2016, International Application No. PCT/JP2014/080984 and Partial translation thereof.
Computer generated English translation of Japanese Application No. 2005-121476A, previously submitted with the IDS dated Mar. 22, 2017.
Office Action of Aug. 22, 2017, for corresponding KR Patent Application No. 10-2015-0162710 and English translation thereof.

* cited by examiner

OPERATION COMMAND GENERATION DEVICE, OPERATION COMMAND GENERATION METHOD, NON-TRANSITORY COMPUTER-READABLE STORAGE MEDIUM, AND PROCESS SYSTEM

INCORPORATION BY REFERENCE

The present disclosure contains subject matter related to that disclosed in Japanese Priority Patent Application JP 2014-237201 filed in the Japan Patent Office on Nov. 21, 2014, the entire contents of which are hereby incorporated by reference.

BACKGROUND OF THE INVENTION

Field of the Invention

The present invention relates to an operation command generation device, an operation command generation method, a non-transitory computer-readable storage medium, and a process system.

Description of the Related Art

In the fields of biochemistry and biotechnology, a work procedure and conditions of the operations to be carried out on a process subject, such as a series of inspections, cultivation, and amplification (hereinafter, these operations are collectively referred to as "experiment"), are commonly referred to as a protocol. A protocol is the information required in order to obtain a result that is reproducible for an experiment or to verify the experiment result.

SUMMARY OF THE INVENTION

According to one aspect of the present invention, there is provided an operation command generation device including: an execution order determination unit configured to determine, based on respective arrangement positions of a plurality of process symbols each representing a process for a process subject on a protocol chart including the plurality of process symbols, an execution order of the plurality of process symbols; and a process symbol conversion unit configured to respectively convert the plurality of process symbols into jobs for a process system including at least a robot so that processes represented by the plurality of process symbols are executed in the execution order determined by the execution order determination unit.

Further, according to another aspect of the present invention, there is provided an operation command generation method including: determining, based on respective arrangement positions of a plurality of process symbols each representing a process for a process subject on a protocol chart including the plurality of process symbols, an execution order of the plurality of process symbols; and respectively converting the plurality of process symbols into jobs for a process system including at least a robot so that processes represented by the plurality of process symbols are executed in the execution order determined in the determining of the execution order.

DESCRIPTION OF THE EMBODIMENTS

Based on the knowledge of the inventors of the present invention, the likelihood of an anticipated result being obtained in a biochemistry or biotechnology experiment, that is, the reproducibility of the experiment, largely depends on the competence of the person conducting the experiment, which can in some cases hinder verification of the reliability of the experiment result, for example. Accordingly, the inventors investigated excluding human factors by using a robot to carry out the experiment.

However, a common format for describing a protocol has not been established yet, and hence each experimenter is considered to describe the protocol in a unique format. Therefore, when an operation of a robot is described based on a certain protocol, for example, an engineer familiar both with the protocol and programming of the operation of the robot is necessary, and moreover, when the format for the protocol is changed, the engineer can no longer use the new format. Thus, describing the operation of the robot based on the protocol is practically unrealistic.

Therefore, the inventors of the present invention invented a novel and creative operation command generation device and the like by carrying out diligent research and development into automatically generating an operation command for causing a robot to perform an experiment based on a protocol. This operation command generation device and the like are described below using an embodiment as an example.

Figure 1:
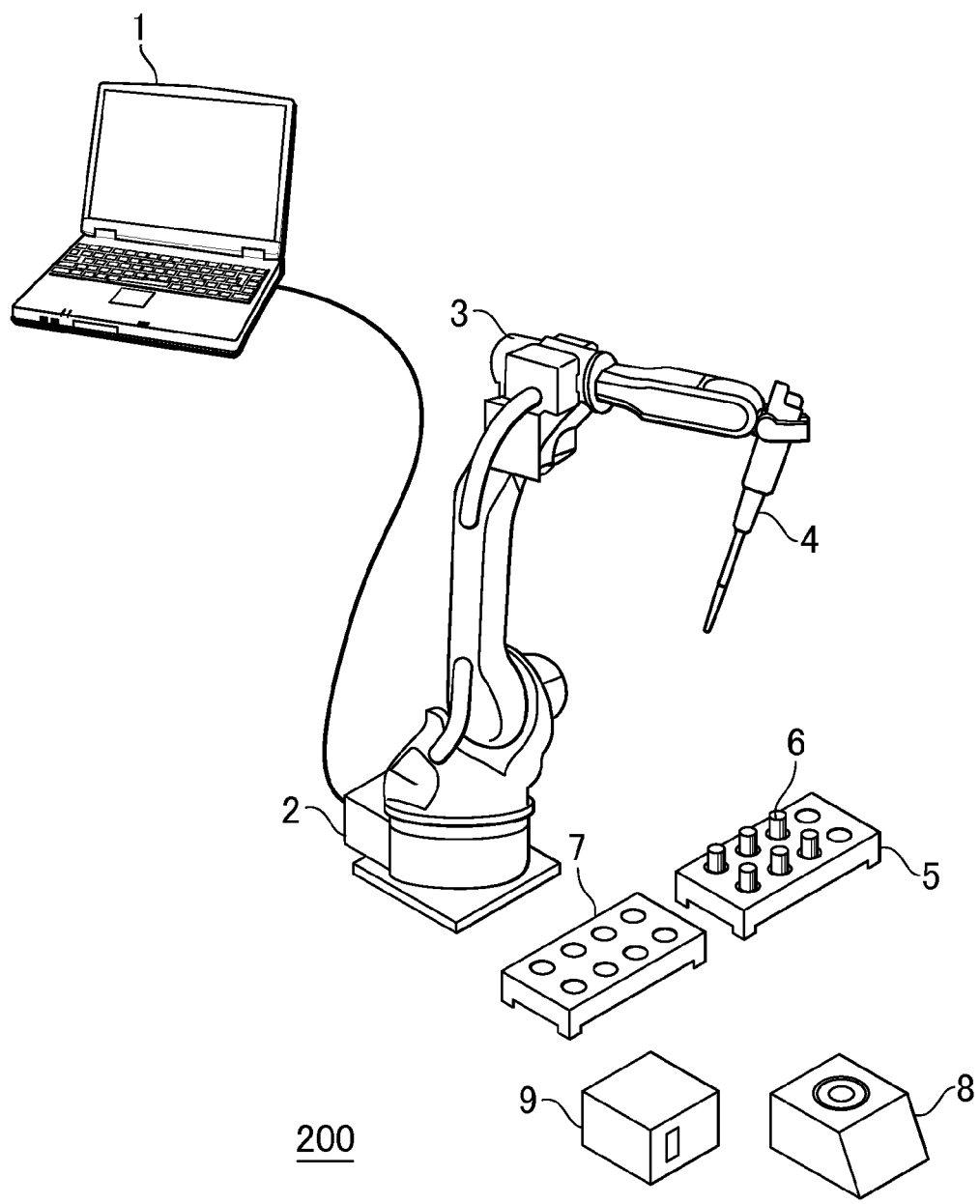
FIG. 1 is a schematic diagram for illustrating a physical configuration of a process system according to an embodiment of the present invention.

FIG. 1 is a schematic diagram for illustrating a physical configuration of a process system 200 according to an embodiment of the present invention. The process system 200 includes an operation command generation device 1 configured to generate an operation command for a robot 3 based on a protocol chart showing a protocol, a robot controller 2 configured to control the robot 3 based on the generated operation command, and the robot 3, which is controlled by the robot controller 2 and is configured to execute an experiment. The operation command generation device 1 itself may be a dedicated device. However, in this case, the operation command generation device 1 is realized by using a common computer. In other words, a commercially-available computer configured to execute a computer program for causing the computer to operate as the operation command generation device 1 is used for the operation command generation device 1. The computer program is in general provided in the form of application software, and is used when installed on the computer. The application software may be provided by recording the application software on a compact disc read-only memory (CD-ROM), a digital versatile disc (DVD) ROM, or another suitable computer-readable information recording medium. Further, the application software may be provided over various information communication networks, such as the Internet. In addition, the functions of the application software may be provided by a server at a remote location over an information communication network, that is, be realized by so-called cloud computing. Still further, the robot controller 2 may be integrated with the robot 3, or in a stand-alone manner. The robot controller 2 causes the robot 3 to execute a desired operation based on an operation command generated by the operation command generation device 1.

The robot 3 is an articulated robot that is configured to carry out processes on a process subject. The robot 3 is capable of manipulating a piece of experiment equipment (which may or may not be shown) such as grasping and manipulating a pipette 4 with an arm. Further, the robot 3 is capable of moving various containers (which may or may not be shown) such as grasping a microtube 6 stored in a tube rack 5 and moving the microtube 6 from the tube rack 5 to a main rack 7 or the like. In this embodiment, when the robot 3 is carrying out a process on the microtube 6, such as injecting the process subject into the microtube 6, the robot 3 moves the microtube 6 to the main rack 7, and carries out the process above the main rack 7. The process system 200 also includes an agitator 8 and a thermostatic bath 9. In the example illustrated in FIG. 1, one example of apiece of equipment to be used when the robot 3 performs the experiment is illustrated. However, the process system 200 may also include other equipment. For example, the process system 200 may include a rack in which a Petri dish is kept, a centrifugal separator, a magnet rack, and the like. Further, the robot 3 is not limited to the type that is illustrated, and the robot 3 may be a dual-arm robot or the like.

Figure 2:
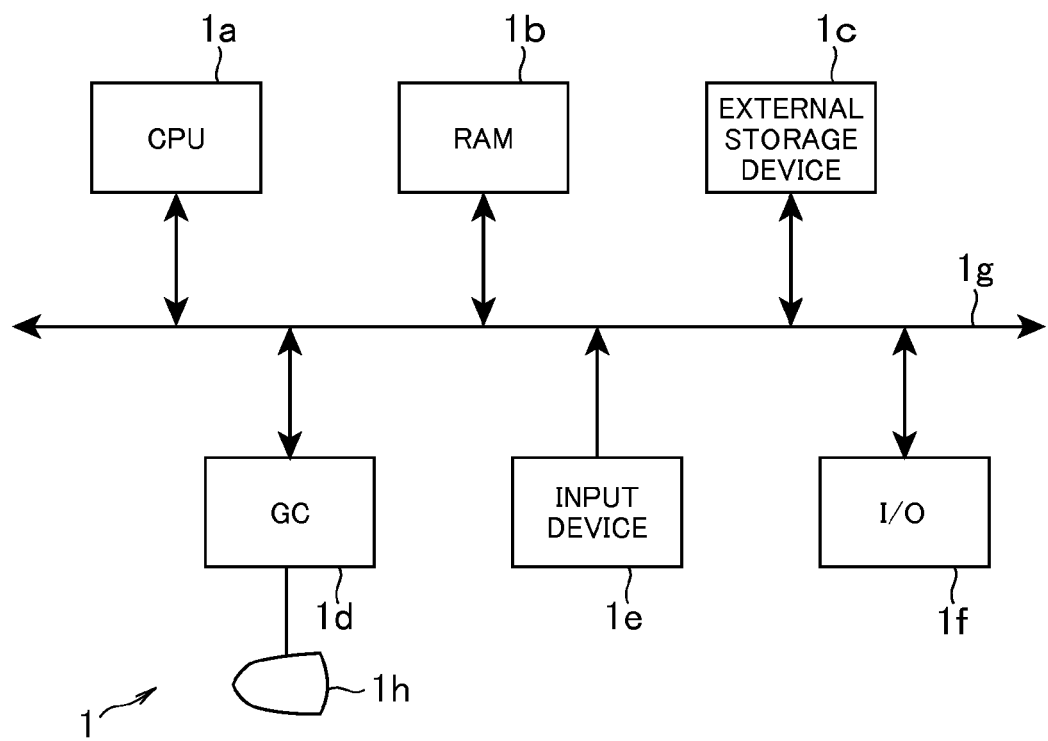
FIG. 2 is a configuration block diagram for illustrating a physical configuration of an operation command generation device according to the embodiment of the present invention.

FIG. 2 is a block diagram for illustrating a physical configuration of the operation command generation device 1 according to the embodiment of the present invention. The configuration illustrated in FIG. 2 is a general computer used as the operation command generation device 1. In the computer, a central processing unit (CPU) 1a, a random access memory (RAM) 1b, an external storage device 1c, a graphics controller (GC) 1d, an input device 1e, and an input/output (I/O) 1f are connected to one another by a data bus 1g so that the devices can exchange electric signals therebetween. In this case, the external storage device 1c is a device capable of statically recording information, such as a hard disk drive (HDD) or a solid state drive (SSD). Further, signals from the GC 1d are output and displayed as an image on a monitor 1h, such as a flat panel display, by which the user visually recognizes the image. The input device 1e is a device, such as a keyboard, a mouse, or a touch panel, by which the user inputs information. The I/O 1f is an interface that allows the operation command generation device 1 to exchange information with an external device.

Figure 3:
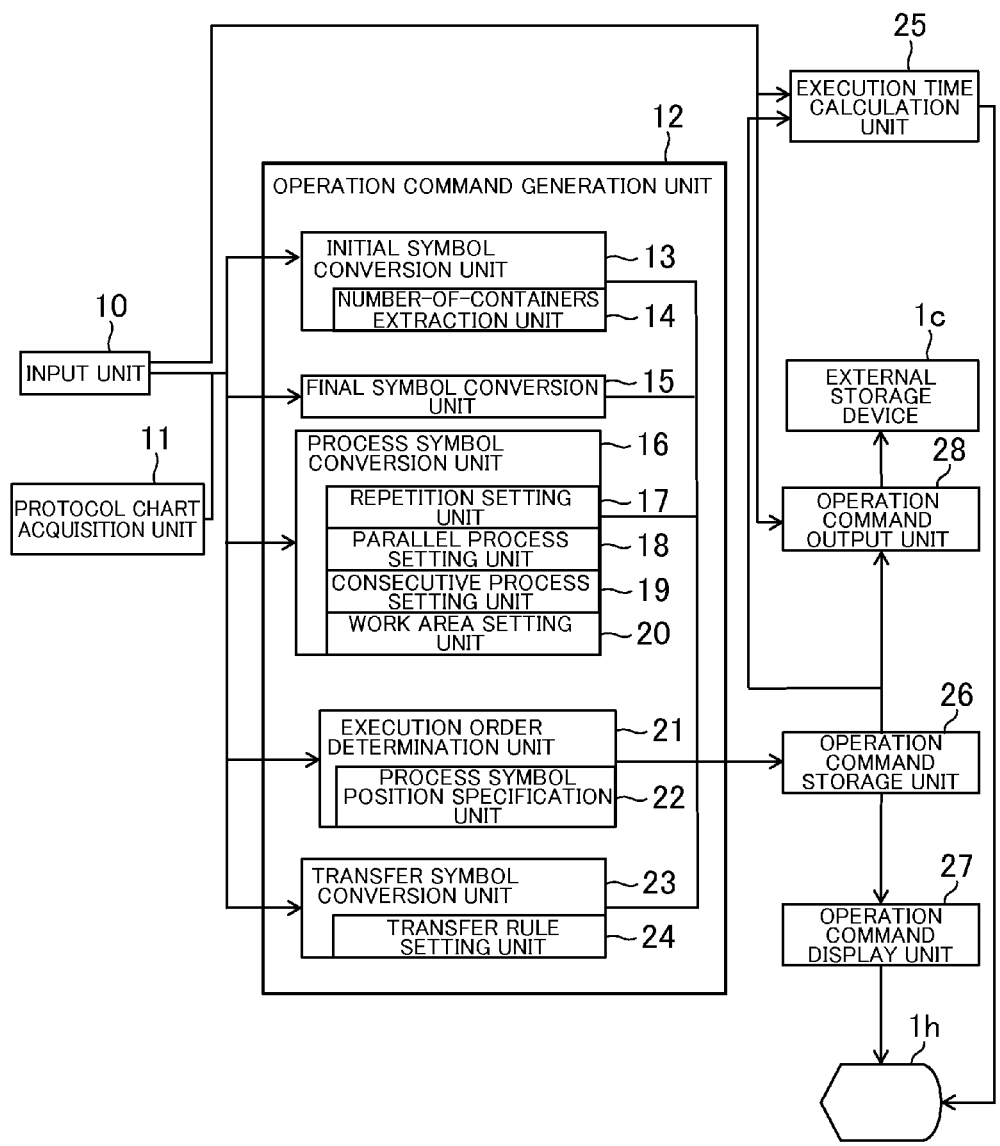
FIG. 3 is a function block diagram of the operation command generation device according to the embodiment of the present invention.

FIG. 3 is a function block diagram of the operation command generation device 1 according to this embodiment. Note that, the function blocks illustrated in FIG. 3 focus on the functions that the operation command generation device 1 has. It is not necessary to have physical configurations that correspond to respective function blocks in a one-to-one manner. Some function blocks may be realized by an information processing device, such as the CPU 1a of the operation command generation device 1, executing specific software. Further, some function blocks may be realized by a specific storage area being allocated to an information storage device, such as the RAM 1b of the operation command generation device 1.

The operation command generation device 1 includes an input unit 10 configured to receive various inputs from a user, and a protocol chart acquisition unit 11 configured to acquire a protocol chart showing a protocol. Further, the operation command generation device 1 includes an operation command generation unit 12 configured to generate an operation command based on the inputs received by the input unit 10 and the protocol chart acquired by the protocol chart acquisition unit 11, and an execution time calculation unit 25 configured to calculate an execution time required for the robot to execute the generated operation command. In addition, the operation command generation device 1 includes an operation command storage unit 26 configured to store electronic data of the operation command currently being generated and operation commands that have been generated, an operation command display unit 27 configured to form the electronic data of the operation commands stored in the operation command storage unit 26 and display the formed electronic data on the monitor 1h, and an operation command output unit 28 configured to output the generated operation command as an electronic file in a format that can be read by the robot.

The input unit 10 is normally configured by the input device 1e illustrated in FIG. 2. However, when the operation command generation device 1 is an application server used in cloud computing, the I/O 1f into which operation information input by the user on a terminal at a remote location is input corresponds to the input unit 10.

The operation command generation unit 12 includes various function blocks for generating an operation command. Although a detailed description is given later along with a description of a generation procedure for the operation command, in this embodiment, the operation command generation unit 12 includes an initial symbol conversion unit 13 configured to convert an initial symbol representing an initial state of a container for containing a process subject into a job of preparing the container. Moreover, the operation command generation unit 12 includes a final symbol conversion unit 15 configured to convert a final symbol representing a final state of a container into a job of executing a final process for the container, and a process symbol conversion unit 16 configured to convert a plurality of process symbols representing processes for a process subject respectively into jobs of the process system so that the processes represented by the plurality of process symbols are executed in an execution order determined by an execution order determination unit 21 described later. Further, the operation command generation unit 12 includes the execution order determination unit 21 configured to determine the execution order of a plurality of process symbols based on respective arrangement positions of the plurality of process symbols on a protocol chart and a transfer symbol conversion unit 23 configured to convert a transfer symbol representing a transfer process of transferring the process subject from a first container to a second container into a job of transferring the process subject from the first container to the second container.

Note that, in this specification, the term job refers to a command, which is issued to a process system including at least a robot, for carrying out a unit process on a container containing a process subject. Further, the term operation command refers to a collection of jobs that combines a plurality of jobs. The operation command generation device 1 is configured to convert individual process symbols represented in a protocol chart into jobs, which are unit processes, and combine the generated jobs while taking into consideration an execution order of the jobs obtained by conversion to generate an operation command for the process system.

The initial symbol conversion unit 13 further includes a number-of-containers extraction unit 14 configured to extract, based on a protocol chart, the number of containers associated with the initial symbol. The process symbol conversion unit 16 receives the number of containers extracted by the number-of-containers extraction unit 14, and converts the process symbol associated with the initial symbol into as many jobs as the number of containers extracted by the number-of-containers extraction unit.

Moreover, the process symbol conversion unit 16 further includes a repetition setting unit 17 configured to set the number of repetitions of a process symbol. The process symbol conversion unit 16 converts the process symbol into a job to be repeated as many times as the number set by the repetition setting unit 17. Moreover, the process symbol conversion unit 16 includes a parallel process setting unit 18 configured to make such a setting that a first process represented by a process symbol and a second process are to be simultaneously executed in parallel. The process symbol conversion unit 16 converts, based on the setting by the parallel process setting unit 18, the process symbol into a job to be executed simultaneously in parallel with the second process. Moreover, the process symbol conversion unit 16 further includes a consecutive process setting unit 19 configured to make such a setting that processes represented by a plurality of process symbols are to be consecutively executed. The process symbol conversion unit 16 converts, based on the setting by the consecutive process setting unit 19, the plurality of process symbols into jobs to be consecutively executed for a signal container. Moreover, the process symbol conversion unit 16 further includes a work area setting unit 20 configured to set a work area in which a process represented by a process symbol is to be executed. The process symbol conversion unit 16 converts the process symbol into a job to be executed in the work area set by the work area setting unit 20.

Moreover, the execution order determination unit 21 includes a process symbol position specification unit 22 configured to specify at least two process symbols equal to each other in the arrangement position in a first direction out of the plurality of process symbols. The execution order determination unit 21 determines the execution order of the at least two process symbols specified by the process symbol position specification unit 22 based on arrangement positions in a second direction intersecting the first direction.

Moreover, the transfer symbol conversion unit 23 further includes a transfer rule setting unit 24 configured to set a transfer rule depending on a relationship between the number of the first containers and the number of the second containers.

Figure 4:
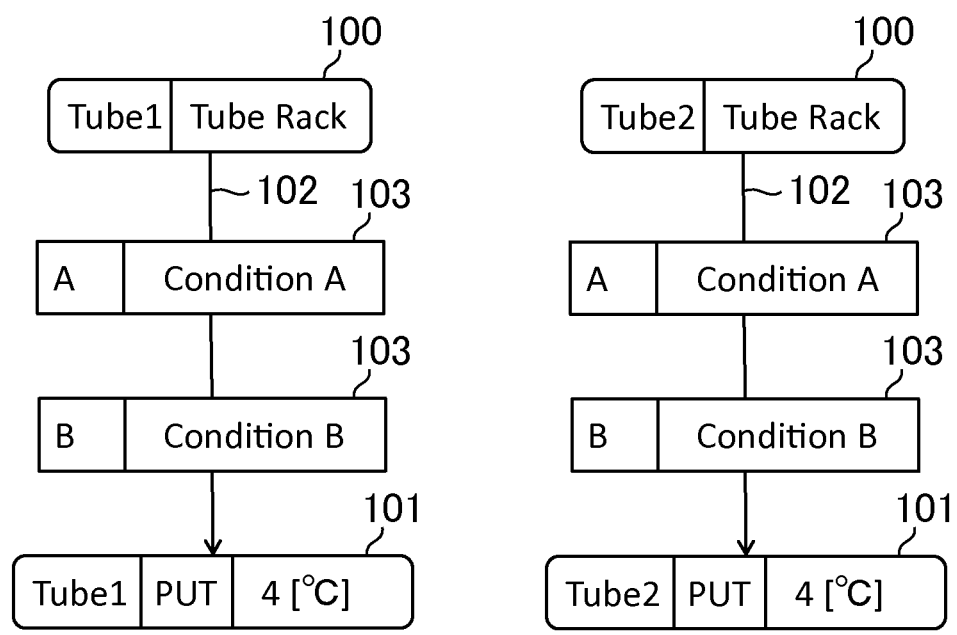
FIG. 4 is a diagram for illustrating a first example of a protocol chart acquired by the operation command generation device according to the embodiment of the present invention.

FIG. 4 is a diagram for illustrating a first example of the protocol chart acquired by the operation command generation device 1 according to this embodiment.

In this specification, the term protocol chart refers to a diagram that is shown in a manner that allows a protocol to be visually understood, and the term protocol refers to the work procedure and conditions of a pre-process and the like to be carried out on a process subject in the field of biochemistry or biotechnology. Further, the term process subject refers to a specimen on which an experiment in the above-mentioned fields is to be performed. In general, the process subject is often a portion of biological tissue, such as a cell, DNA, or the like. The experiment is generally carried out by placing the process subject in a piece of equipment that is particularly suited to the experiment, such as a microtube (centrifuge tube), a Petri dish, or a microplate (microtiter plate). However, when the term container is used by itself in this specification, the term refers to all of those pieces of equipment suitable for containing the process subject in the experiment.

Further, for convenience, the upward direction in FIG. 4 is referred to as a first direction, and the direction intersecting the first direction is referred to as a second direction. It is not necessary for the angle of intersection between the first direction and the second direction to be a right angle. However, in this case, the first direction and the second direction are perpendicular to each other. As a result, the second direction is the axis in the horizontal direction in FIG. 4.

In the protocol chart of this example, basically, an initial symbol 100 representing an initial state of the container containing the process subject and a final symbol 101 representing a final state of the container are arranged in the first direction. The initial symbol 100 and the final symbol 101 are connected in the first direction by a procedure line 102 heading from the initial symbol 100 to the final symbol 101. A process symbol 103 representing an individual process to be carried out on the container is arranged along the procedure line 102. In the first example illustrated in FIG. 4, there are a set of the initial symbol 100 and final symbol 101 in which "Tube 1" is written and the procedure line 102 connecting the initial symbol 100 and the final symbol 101 and a set of the initial symbol 100 and final symbol 101 in which "Tube 2" is written and the procedure line 102 connecting the initial symbol 100 and the final symbol 102. In this case, the procedure line 102 represents the procedure to be carried out by the process as an arrow line. In other words, the protocol chart of this example means that first the jobs represented by the initial symbols 100, in which "Tube 1" and "Tube 2" are respectively written, are carried out, then the jobs represented by the process symbols 103, in which "A" is written for "Tube 1" and "Tube 2", are carried out, subsequently the jobs represented by the process symbols 103, in which "B" is written for "Tube 1" and "Tube 2", are carried out, and lastly the jobs represented by the final symbols 101, in which "Tube 1" and "Tube 2" are respectively written, are carried out.

According to this embodiment, the execution order determination unit 21 determines an execution order of a plurality of process symbols 103 based on respective arrangement positions of the plurality of process symbols 103 on the protocol chart. On this occasion, in order to uniquely acquire a protocol from the protocol chart, it is desired to determine an execution order of process symbols 103 arranged at the same position in the first direction so as to prioritize the processes.

According to this embodiment, the process symbol position specification unit 22 specifies at least two process symbols the same in the arrangement position in the first direction (upward direction of the figure) out of a plurality of process symbols. Then, the execution order determination unit 21 determines the execution order of the at least two process symbols specified by the process symbol position specification unit 22 based on the arrangement positions in the second direction (horizontal direction of the figure). Specifically, the execution order determination unit 21 determines the execution order so as to execute earlier a process symbol arranged on the left side of the figure, and execute later a process symbol arranged on the right side of the figure.

A description is now given of how the respective elements of the first example of the protocol chart illustrated in FIG. 4 are converted into jobs by the operation command generation device 1.

First, the protocol chart is acquired by the protocol chart acquisition unit 11 of the operation command generation device 1, an initial symbol 100 which is written at the upper most line of the protocol chart and in which "Tube 1" is written and an initial symbol 100 which is written at the upper most line of the protocol chart and in which "Tube 2" is written are converted by the initial symbol conversion unit 13 into jobs of each preparing a container for containing a process subject. "Tube 1" written on the left side of the initial symbol 100 represents a first microtube, "Tube 2" on the left side of the initial symbol 100 represents a second microtube, and "Tube Rack" on the right side of the initial symbol 100 represents a device in which the microtubes are kept, and is the tube rack 5 on this occasion. Note that, the first microtube and the second microtube may be microtubes of the same type. Moreover, the process for the container is executed on the main rack 7 in principle, and hence the job of preparing the container means a job of moving the container to the main rack 7. Thus, the initial symbol conversion unit 13 converts the initial symbol 100 in which "Tube 1" is written to a job of using the arm of the robot 3 to move the first microtube 1 from a first storage location in the tube rack 5 to a first storage location in the main rack 7. Moreover, the initial symbol conversion unit 13 converts the initial symbol 100 in which "Tube 2" is written to a job of using the arm of the robot 3 to move the second microtube from a second storage location in the tube rack 5 to a second storage location in the main rack 7. On this occasion, the first and second microtubes may be moved one at a time, or an arm capable of holding a plurality of microtubes may be employed as the arm of the robot 3 so as to move the microtubes simultaneously.

Next, the process symbol 103 in which "A" is written, which is connected by the procedure line 102 to the initial symbol 100 in which "Tube 1" is written, is read. In this case, the process symbol 103 in which "A" is written represents an arbitrary process to be carried out on the microtube under Condition A. In this example, a specific content of the process is not exemplified, but a specific example of the process is described in a second example of the protocol chart.

A process symbol 103 in which "A" is written for "Tube 1" and a process symbol 103 in which "A" is written for "Tube 2" are arranged at the same position in the first direction. Therefore, the process symbol position specification unit 22 specifies the process symbol 103 in which "A" is written for "Tube 1" and the process symbol 103 in which "A" is written for "Tube 2". The execution order determination unit 21 receives this specification to determine the execution order of the jobs based on the positions in the second direction. In other words, the execution order determination unit 21 makes such a determination that the job represented by the process symbol 103 in which "A" is written for "Tube 1" located on the left side of the figure is executed first, and the job represented by the process symbol 103 in which "A" is written for "Tube 2" located on the right side of the figure is executed second. The process symbol conversion unit 16 receives this determination, and converts the process symbols 103 in which "A" is written for "Tube 1" and "Tube 2" into jobs of executing the process "A" for "Tube 1" first and then executing the process "A" for "Tube 2" second.

Then, process symbols 103 in which "B" is written are converted into jobs in accordance with the direction (first direction) of the procedure lines 102. On this occasion, the process symbol 103 in which "B" is written represents an arbitrary process executed under Condition B for the microtube. The process symbol position specification unit 22 also specifies the process symbols 103 in which "B" is written as process symbols equal to each other in the arrangement position in the first direction. Then, the execution order determination unit 21 makes such a determination that the job represented by the process symbol 103 in which "B" is written for "Tube 1" located on the left side of the figure is executed first, and the job represented by the process symbol 103 in which "B" is written for "Tube 2" located on the right side of the figure is executed second. The process symbol conversion unit 16 receives this determination, and converts the process symbols 103 in which "B" is written for "Tube 1" and "Tube 2" into jobs of executing the process "B" for "Tube 1" first and then executing the process "B" for "Tube 2" second.

Finally, a final symbol 101 in which "Tube 1" is written and a final symbol 101 in which "Tube 2" is written are converted by the final symbol conversion unit 15 into jobs of each executing a final process for the container. On this occasion, "PUT" means keeping a microtube in a device, and the final symbol conversion unit 15 converts the final symbols 101 in which "Tube 1" and "Tube 2" are respectively written into jobs of respectively keeping the first and second microtubes in the thermostatic bath 9 at 4° C.

The execution order of the jobs is uniquely determined by defining the execution order of the process symbols based on the arranged positions on the protocol chart in this way, and the operation command used to cause the robot to carryout an experiment can be automatically generated. Moreover, even if the process symbols are arranged at positions equal to each other in the first direction, by defining the execution order based on positions in the second direction intersecting the first direction, an execution order of the jobs is uniquely determined from the protocol chart described two-dimensionally, and the operation command can be automatically generated.

Figure 5:
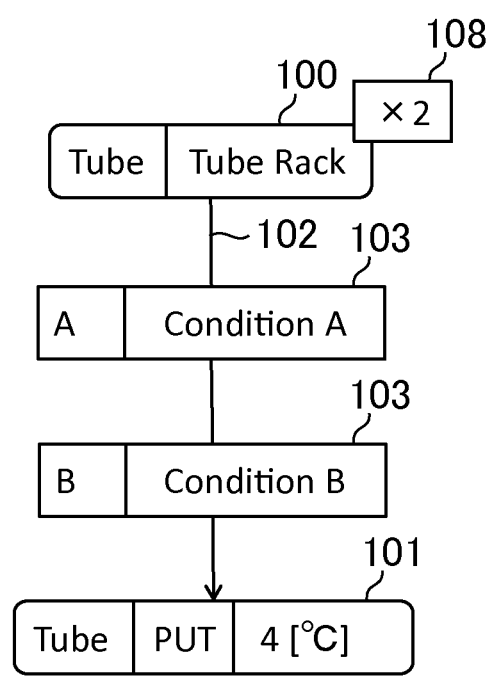
FIG. 5 is a diagram for illustrating a protocol chart equivalent to the first example of the protocol chart.

FIG. 5 is a diagram for illustrating a protocol chart equivalent to the first example of the protocol chart. On the protocol chart illustrated in FIG. 5, a number-of-containers symbol 108 is arranged so as to overlap the initial symbol 100 in which "Tube" is written. The number-of-containers symbol 108 explicitly represents the number of containers associated with the initial symbol 100, and based on characters "×2", explicitly represents that the initial symbol 100 in which "Tube" is written is converted into a job of preparing two microtubes and a process symbol 103 connected to the initial symbol 100 by a procedure line 102 is converted into jobs of executing a process for the two microtubes.

According to this embodiment, the number-of-containers extraction unit 14 extracts the number of containers associated with an initial symbol. Note that, the number of containers associated with the initial symbol is not limited to the number explicitly represented by the number-of-containers symbol 108 as illustrated in FIG. 5, and, for example, may be a number set as a parameter accompanying the initial symbol. When the number-of-containers extraction unit 14 extracts the number of containers, at least the process symbol conversion unit 16 converts the process symbol associated with the initial symbol into as many jobs as the number of containers extracted by the number-of-containers extraction unit 14.

A description is now given of how the respective elements of the protocol chart illustrated in FIG. 5 are converted into jobs by the operation command generation device 1.

First, the number-of-containers extraction unit 14 extracts the number of containers associated with the initial symbol 100 in which "Tube" is written. In other words, the number-of-containers extraction unit 14 extracts the number of containers, namely, 2, from the number-of-containers symbol 108 in which "×2" is written.

Then, the initial symbol conversion unit 13 converts the initial symbol 100 in which "Tube" is written and with which the number of containers is associated into the jobs of preparing the first and second microtubes. Moreover, the process symbol conversion unit 16 converts the process symbols associated with the initial symbol in which "Tube" is written, namely, the process symbol 103 in which "A" is written and the process symbol 103 in which "B" is written, into jobs of respectively executing Processes A and B for the first and second microtubes. On this occasion, while two sets including the initial symbol 100 in which "Tube" is written, the final symbol 101, and the procedure line 102 connecting both of the symbols to each other are considered to be arranged as being separated from each other in the second direction and arranged at the same position in the first direction, the execution order of the jobs is defined by the execution order determination unit 21 and the process symbol position specification unit 22. In other words, the execution order of the jobs is defined while the protocol chart of FIG. 5 is replaced by the first example of the protocol chart. As a result, the process symbol 103 in which "A" is written and the process symbol 103 in which "B" is written are converted by the process symbol conversion unit 16 into jobs of executing Process A for the first microtube, executing Process A for the second microtube, executing Process B for the first microtube, and executing Process B for the second microtube. Finally, the final symbol conversion unit 15 converts the final symbol 101 in which "Tube" is written into jobs of keeping the first and second microtubes in the thermostatic bath 9 at 4° C. An operation command generated as a result is the same as an operation command generated for the first example of the protocol chart illustrated in FIG. 4.

If processes for a plurality of containers are described in a protocol chart without omissions, the protocol chart extends in the horizontal direction of the figure as the number of containers increases, and readability of the protocol chart is degraded. Therefore, processes having the same content for a plurality of containers of the same type are preferably described in a simple manner. With the operation command generation device 1 according to this embodiment, even for a protocol chart simply describing processes for a plurality of containers of the same type by presenting the number of the containers, each of the plurality of containers is considered as a protocol chart describing a set including an initial symbol 100, a final symbol 101, and a procedure line 102 connecting both the symbols to each other, and an operation command for the plurality of containers is generated.

Figure 6:
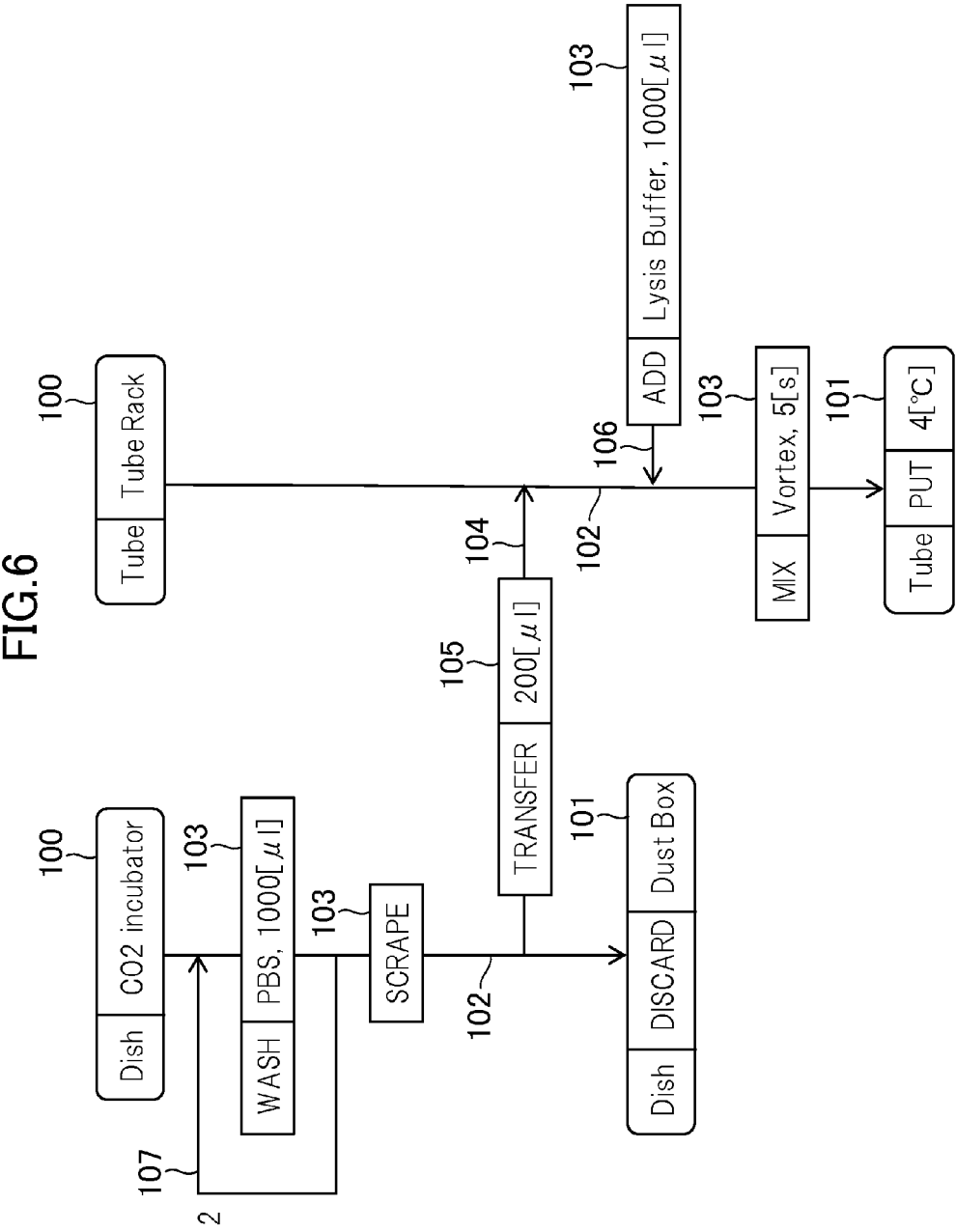
FIG. 6 is a diagram for illustrating a second example of the protocol chart acquired by the operation command generation device according to the embodiment of the present invention.

FIG. 6 is a diagram for illustrating a second example of the protocol chart acquired by the operation command generation device 1 according to the embodiment of the present invention. The second example represents specific contents of processes executed for containers.

In the second example, the initial symbol 100 and the final symbol 101 in which "Dish" is written, and the procedure line 102 connecting the initial symbol 100 and the final symbol 101, and the initial symbol 100 and the final symbol 101 in which "Tube" is written, and the procedure line 102 connecting the initial symbol 100 and the final symbol 101, are arranged at positions offset from each other in the second direction.

In this example, a process subject is transferred from "Dish" to "Tube", and a transfer line 104 connecting the procedure line 102 and the procedure line 102 to each other in the second direction is arranged and a transfer symbol 105 in which "TRANSFER" is written representing the transfer is arranged on the transfer line 104. The transfer line 104 explicitly represents a transfer direction of the process subject, and, on this occasion, is an arrow, to thereby represent a transfer direction thereof.

Moreover, in this example, a process symbol 103 in which "ADD" is written meaning addition and the procedure line 102 for "Tube" are connected to each other by an addition line 106 in the second direction. The addition line 106 is also an arrow directing to the procedure line 102 so as to explicitly represent addition to the container.

Moreover, in this example, a repetition line 107 is arranged. The repetition line 107 is drawn so as to branch from the procedure line 102 to extend in the second direction, bend toward and to extend in the first direction, a top direction on this occasion, further bend in the second direction, and reconnect to the procedure line 102, and "2" representing the number of the repetitions is written by the side of the repetition line 107. Note that, a process symbol is preferably not arranged at a position the same in the first direction and separated in the second direction as and from the position at which the repetition line 107 is arranged. This is because it is difficult to uniquely define the execution order between the process symbol associated with the repetition line 107 and the process symbol arranged so as to be separated in the second direction, and even if the order is defined, the order is difficult to intuitively understand.

A description is now given of how the respective elements of the second example of the protocol chart exemplified in FIG. 6 are converted into jobs by the operation command generation device 1.

First, the protocol chart is acquired by the protocol chart acquisition unit 11 of the operation command generation device 1, and the initial symbol 100 in which "Dish" is written and which is written on the uppermost line of the protocol chart is converted by the initial symbol conversion unit 13 into a job of preparing a container for containing a process subject. "Dish" written on a left side of the initial symbol 100 represents a Petri dish, and "CO2 incubator" written on aright side of the initial symbol 100 represents a device in which the Petri dish is kept, and, in this example, is a carbon dioxide gas atmosphere incubator. The initial symbol conversion unit 13 converts the initial symbol 100 in which "Dish" is written into a job of moving the Petri dish, which is kept in the carbon dioxide gas atmosphere incubator, and in which, for example, a biological tissue is cultivated, to a predetermined location by using the arm of the robot 3 to prepare for a process to be executed for the Petri dish.

Moreover, the initial symbol conversion unit 13 converts an initial symbol 100 in which "Tube" is written and which is written on the upper most line of the protocol chart into a job of preparing a container for containing the process subject. As described above, "Tube" represents the microtube, and "Tube Rack" represents the tube rack 5. The initial symbol conversion unit 13 converts the initial symbol 100 in which "Tube" is written into a job of moving the microtube kept in the tube rack 5 to the main rack 7 by using the arm of the robot 3 to prepare for a process to be executed for the microtube.

Subsequently to the job of preparing the container, a job represented by a process symbol 103 in which "WASH" is written is executed. A left side of this process symbol 103 represents a type of the process, and a right side thereof represents a condition for the process. On this occasion, "WASH" means cell washing, and "PBS, 1,000 [µl]" means that 1,000 µl of phosphate buffered saline is used for the cell washing. This cell washing is carried out twice in accordance with the repetition line 107. The repetition setting unit 17 sets the number (2) of the repetition of the process symbol 103 in which "WASH" is written. The process symbol conversion unit 16 receives this setting, and converts the process symbol 103 in which "WASH" is written into a job of repeating the cell washing process twice.

Then, a job represented by a process symbol 103 in which "SCRAPE" is written is executed. This process is so-called scraping, and represents an operation of using a scraper to scrape a bottom of a Petri dish, to thereby scrape off a process subject such as cells adhered to the Petri dish. Thus, the process symbol conversion unit 16 converts the process symbol 103 in which "SCRAPE" is written into a job of using the arm of the robot 3 to hold the scraper, and using the scraper to carry out scraping for the Petri dish.

Further, a job represented by a transfer symbol 105 in which "TRANSFER" is written is executed. The transfer symbol conversion unit 23 converts the transfer symbol 105 in which "TRANSFER" is written into a job of using the pipette 4 held by the arm of the robot 3 to transfer 200 µl of the process subject scraped off from the Petri dish, which is the first container, to the microtube, which is the second container.

The Petri dish after the transfer of the process subject is brought into a final state represented by a final symbol 101 in which "Dish" is written in accordance with the procedure line 102. On this occasion, "DISCARD" written in a center part of the final symbol 101 represents an operation of discarding the Petri dish, and "Dust Box" written on a right side of the final symbol 101 represents a discard destination thereof. The final symbol conversion unit 15 converts the final symbol 101 in which "Dish" is written into a job of executing a discard process (discarding the Petri dish into the dust box), which is a final process, for the Petri dish held by the arm of the robot 3.

On the other hand, regarding the microtube, further in accordance with the procedure line 102, a process represented by a process symbol 103 in which "ADD" is written is executed. The process symbol 103 in which "ADD" is written represents a process of adding 1,000 µl of a cell lysis buffer as indicated by a condition written on a right side thereof. The process symbol conversion unit 16 converts the process symbol 103 in which "ADD" is written into a job of using the pipette 4 held by the arm of the robot 3 to add 1,000 µl of the cell lysis buffer to the microtube.

Further, a process represented by a process symbol 103 in which "MIX" is written is executed. This process means agitation of a content, and "Vortex, 5 [s]" written as a process condition means an agitation process for five seconds with an agitator. Thus, the process symbol conversion unit 16 converts the process symbol 103 in which "MIX" is written into a job of setting the microtube held by the arm of the robot 3 to the agitator 8, to thereby agitate the content for five seconds.

Finally, the microtube is brought into a final state represented by a final symbol 101 in which "Tube" is written. On this occasion, "PUT" means keeping the microtube in a device, and hence the microtube is stored and kept in the thermostatic bath at 4° C. The final symbol conversion unit 15 converts the final symbol 101 in which "Tube" is written into a job of executing a storage process of storing the microtube in the thermostatic bath 9 at 4° C., which is a final process, for the microtube held by the arm of the robot 3.

As described above, the operation command generation device 1 according to this embodiment converts respective elements to specific jobs based on an execution order uniquely defined by arrangement positions of the respective elements on a protocol chart, to thereby generate an operation command, which is a set of the jobs. Moreover, when a protocol chart using a repetition line for an omitted description is given, jobs of repeating the same process can be generated. Further, when a protocol chart including a transfer line and a transfer symbol is given, a job of transferring a process subject from one container to another container can be generated.

Figure 7:
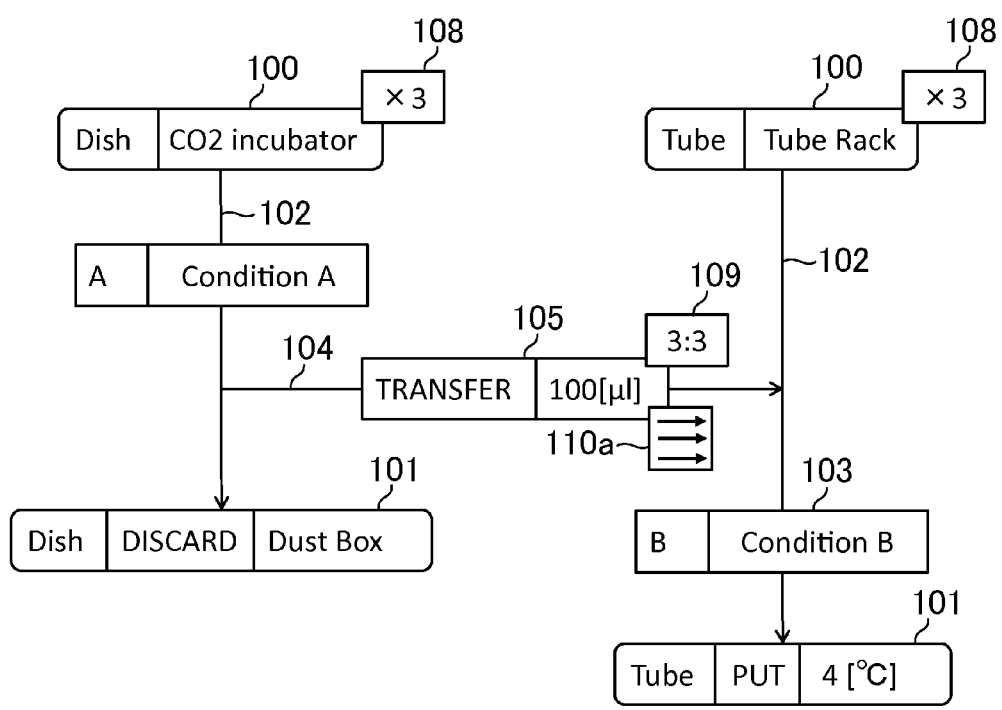
FIG. 7 is a diagram for illustrating a third example of the protocol chart acquired by the operation command generation device according to the embodiment of the present invention.

FIG. 7 is a diagram for illustrating a third example of the protocol chart acquired by the operation command generation device 1 according to this embodiment. A protocol represented by the third example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×3" is associated with an initial symbol 100 of "Dish" representing preparation of Petri dishes. The number-of-containers symbol 108 represents that the same process is executed for the same type of three Petri dishes. Moreover, a number-of-containers symbol 108 including characters "×3" is associated with an initial symbol 100 of "Tube" representing preparation of microtubes. The number-of-containers symbol 108 represents that the same process is executed for the same type of three microtubes.

The protocol chart of this example includes a transfer symbol 105 representing a transfer process. Moreover, a number-of-transfers symbol 109 is associated with the transfer symbol 105. The number-of-transfers symbol 109 includes the number (3) of the Petri dishes, which are the first containers, and the number (3) of the microtubes, which are the second containers. Specifically, the number-of-transfers symbol 109 includes characters "3:3", and the number of containers of a transfer source is represented on a left side of the characters, and the number of containers of a transfer destination is represented on a right side of the characters.

A first pictogram 110a is associated with the transfer symbol 105. The first pictogram 110a is a sign of three arrows extending from the left toward the right of the figure. The number-of-transfers symbol 109 and the first pictogram 110a concisely represent a first transfer rule for the case in which the process subject is transferred from the three Petri dishes, which are the first containers, to the three microtubes, which are the second containers. Hereinafter, for a description of the transfer rule, the three Petri dishes are referred to first to third Petri dishes, and the three microtubes are referred to as first to third microtubes. In this example, the first transfer rule means a transfer rule in which 100 µl of the process subject is transferred from the first Petri dish to the first microtube, 100 µl of the process subject is transferred from the second Petri dish to the second microtube, and 100 µl of the process subject is transferred from the third Petri dish to the third microtube. In this example, the number-of-transfers symbol 109 and the first pictogram 110a enable intuitive recognition of the first transfer rule, but the first transfer rule does not always need to be explicitly represented on the protocol chart. Moreover, one of the number-of-transfers symbol 109 and the first pictogram 110a may be represented on the protocol chart.

The transfer rule setting unit 24 sets the first transfer rule when the number of the first containers (Petri dishes in this example) and the number of the second containers (microtubes in this example) are equal to each other. Then, the transfer symbol conversion unit 23 converts, based on the first transfer rule, the transfer symbol 105 into a job of repeating the process of transferring the process subject from the first container to the second container in a one-to-one manner as many times as the number of the containers. In this example, the number of Petri dishes, which are the first containers, and the number of the microtubes, which are the second containers, are equal to each other, and the transfer rule setting unit 24 thus sets the first transfer rule. Moreover, the transfer symbol conversion unit 23 converts the transfer symbol 105 into a job of repeating, for three times, the process of transferring 100 µl of the process subject from the Petri dish to the microtube each time in a one-to-one manner based on the first transfer rule. In this way, with the transfer symbol conversion unit 23 and the transfer rule setting unit 24 according to this embodiment, the job of transferring the process subject between the containers the same in the number is generated based on the transfer rule. In particular, as in this example, if the transfer rule setting unit 24 sets the transfer rule based on the number of the first containers and the number of the second containers, the transfer rule suitable for execution of the protocol is automatically set without fully explicitly representing the transfer rule by a person who produces a protocol chart, resulting in an increase in productivity of the protocol chart. Naturally, if a transfer rule is explicitly represented on the protocol chart, the transfer rule setting unit 24 sets a transfer rule based on the explicitly represented transfer rule. The same holds true for various examples of the transfer rule described below.

Figure 8:
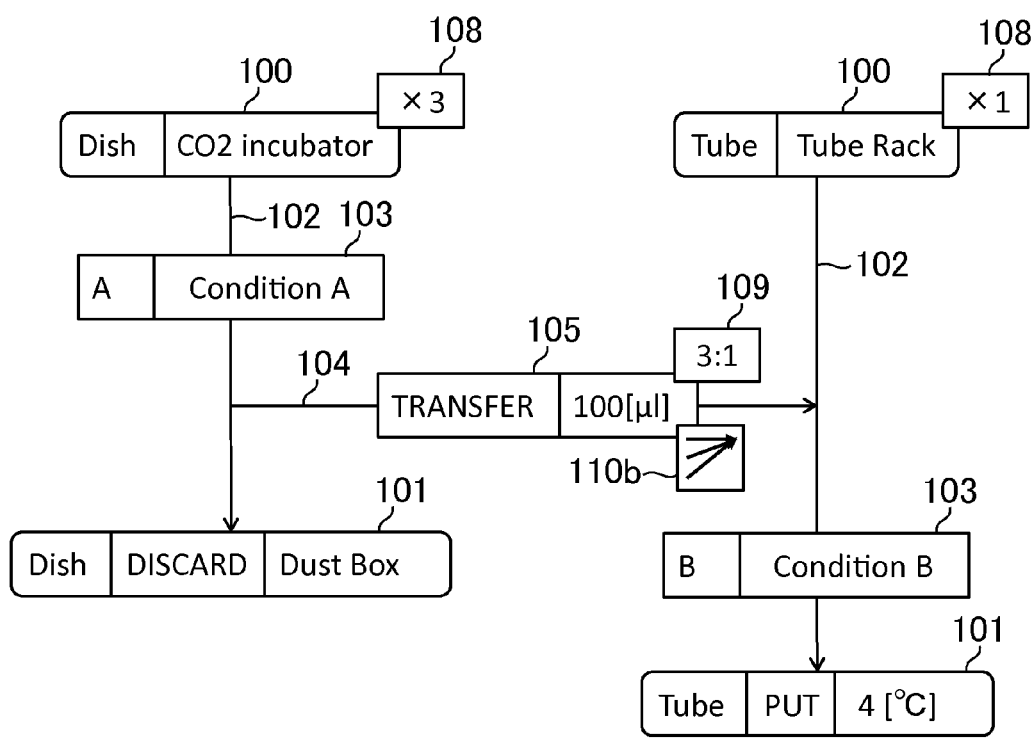
FIG. 8 is a diagram for illustrating a fourth example of the protocol chart acquired by the operation command generation device according to the embodiment of the present invention.

FIG. 8 is a diagram for illustrating a fourth example of the protocol chart acquired by the operation command generation device 1 according to this embodiment. A protocol represented by the fourth example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×3" is associated with an initial symbol 100 of "Dish" representing preparation of Petri dishes. The number-of-containers symbol 108 represents that the same process is executed for the same type of three Petri dishes. Moreover, a number-of-containers symbol 108 including characters "×1" is associated with an initial symbol 100 of "Tube" representing preparation of microtubes. The number-of-containers symbol 108 represents that a process is executed for a single microtube.

The protocol chart of this example includes a transfer symbol 105. A number-of-transfers symbol 109 is associated with the transfer symbol 105. The number-of-transfers symbol 109 includes the number (3) of the Petri dishes, which are the first containers, and the number (1) of the microtubes, which are the second containers. Specifically, the number-of-transfers symbol 109 includes characters "3:1", and the number of containers of a transfer source is represented on a left side of the characters, and the number of containers of a transfer destination is represented on a right side of the characters.

A second pictogram 110b is associated with the transfer symbol 105. The second pictogram 110b is a sign of three arrows extending from three points arranged on the left side of the figure toward one point on the right side of the figure so as to converge on the one point. The number-of-transfers symbol 109 and the second pictogram 110b concisely represent a second transfer rule for the case in which the process subject is transferred from the three Petri dishes, which are the first containers, to the one microtube, which is the second container. In this example, the second transfer rule means a transfer rule of collecting 100 µl of the process subject from each of the first to third Petri dishes, which totals 300 µl, to the single microtube.

The transfer rule setting unit 24 sets the second transfer rule when the number of the first containers is at least two and the number of the second containers is one. Then, the transfer symbol conversion unit 23 converts, based on the second transfer rule, the transfer symbol 105 into a job of repeating the process of transferring the process subject from the first container to the second container for all the first containers. In this example, the number of Petri dishes, which are the first containers, is at least two, and the number of the microtubes, which are the second containers, is one, and the transfer rule setting unit 24 thus sets the second transfer rule. Moreover, the transfer symbol conversion unit 23 converts the transfer symbol 105 into a job of repeating, for all the Petri dishes, the process of transferring the process subject from the Petri dish to the microtube based on the second transfer rule. In this way, with the transfer symbol conversion unit 23 and the transfer rule setting unit 24 according to this embodiment, a job of collecting the process subject from a plurality of containers to a single container is generated.

Figure 9:
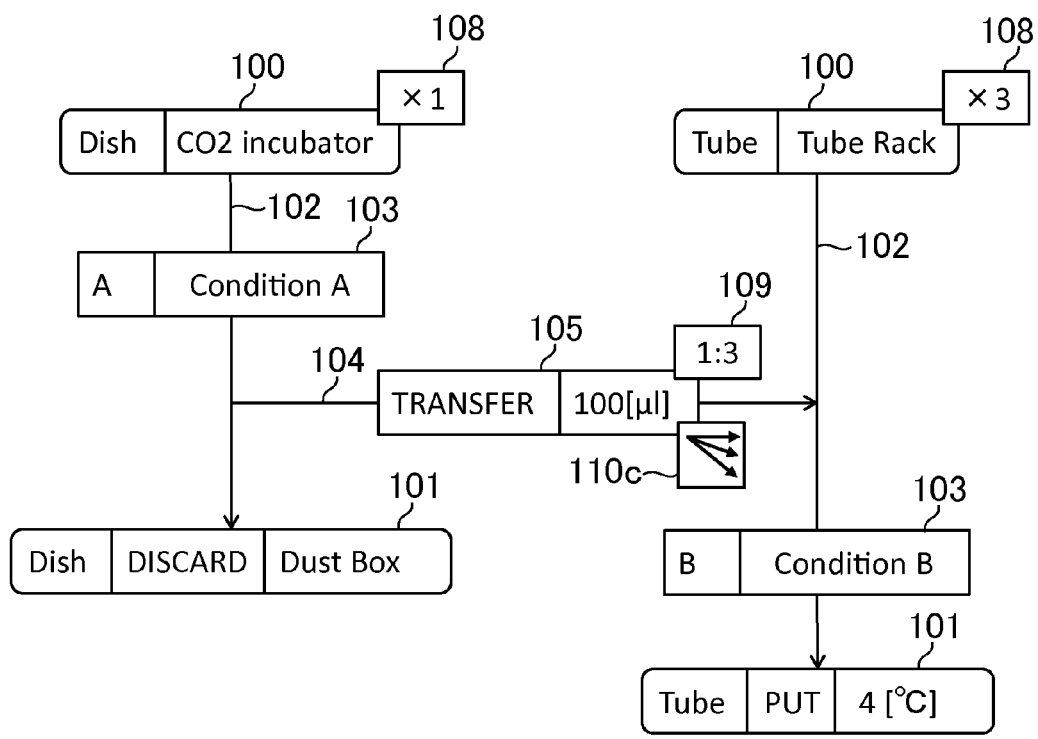
FIG. 9 is a diagram for illustrating a fifth example of the protocol chart acquired by the operation command generation device according to the embodiment of the present invention.

FIG. 9 is a diagram for illustrating a fifth example of the protocol chart acquired by the operation command generation device 1 according to this embodiment. A protocol represented by the fifth example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×1" is associated with an initial symbol 100 of "Dish" representing preparation of a Petri dish. The number-of-containers symbol 108 represents that a process is executed for a single Petri dish. Moreover, a number-of-containers symbol 108 including characters "×3" is associated with an initial symbol 100 of "Tube" representing preparation of microtubes. The number-of-containers symbol 108 represents that the same process is executed for the same type of three microtubes.

The protocol chart of this example includes a transfer symbol 105. A number-of-transfers symbol 109 is associated with the transfer symbol 105. The number-of-transfers symbol 109 includes the number (1) of the Petri dishes, which are the first containers, and the number (3) of the microtubes, which are the second containers. Specifically, the number-of-transfers symbol 109 includes characters "1:3", and the number of containers of a transfer source is represented on a left side of the characters, and the number of containers of a transfer destination is represented on a right side of the characters.

A third pictogram 110*c* is associated with the transfer symbol 105. The third pictogram 110*c* is a sign of three arrows extending from one point arranged on the left side of the figure toward three points on the right side of the figure so as to diverge toward the three points. The number-of-transfers symbol 109 and the third pictogram 110*c* concisely represent a third transfer rule for the case in which the process subject is transferred from the one Petri dish, which is the first container, to the three microtube, which are the second containers. In this example, the third transfer rule means a transfer rule of transferring a process subject to the first microtube, the second microtube, and the third microtube in a distributive manner.

The transfer rule setting unit 24 sets the third transfer rule when the number of the first containers is one and the number of the second containers is at least two. Then, the transfer symbol conversion unit 23 converts, based on the third transfer rule, the transfer symbol 105 into a job of repeating the process of transferring the process subject from the first container to the second container for all the second containers. In this example, the number of Petri dishes, which are the first containers, is one, and the number of the microtubes, which are the second containers, is at least two, and the transfer rule setting unit 24 thus sets the third transfer rule. Moreover, the transfer symbol conversion unit 23 converts the transfer symbol 105 into a job of repeating, for all the microtubes, the process of transferring the process subject from the Petri dish to the microtube based on the third transfer rule. On this occasion, a method of distributing the process subject to the respective microtubes is an equal distribution in principle, but a ratio of the distribution may be set by a user. Moreover, a job may be converted so as to transfer the entire amount of the process subject in the first container by omitting a description of a transfer amount on the transfer symbol 105, or by describing the transfer of the entire amount (for example, "All"). Even in this case, the method of distributing the process subject to the respective microtubes is the equal distribution in principle, but the ratio of the distribution may be set by the user. Moreover, if the pipette is used to suck the entire amount, an error may occur, such as a suction of the outside air or the like, and hence when the transfer of the entire amount is instructed, an amount smaller by a certain degree than the entire amount recognized on the protocol chart, such as 90% of the process subject, may be transferred. In this way, with the transfer symbol conversion unit 23 and the transfer rule setting unit 24 according to this embodiment, a job of distributing the process subject from a single container to a plurality of containers is generated.

Figure 10:
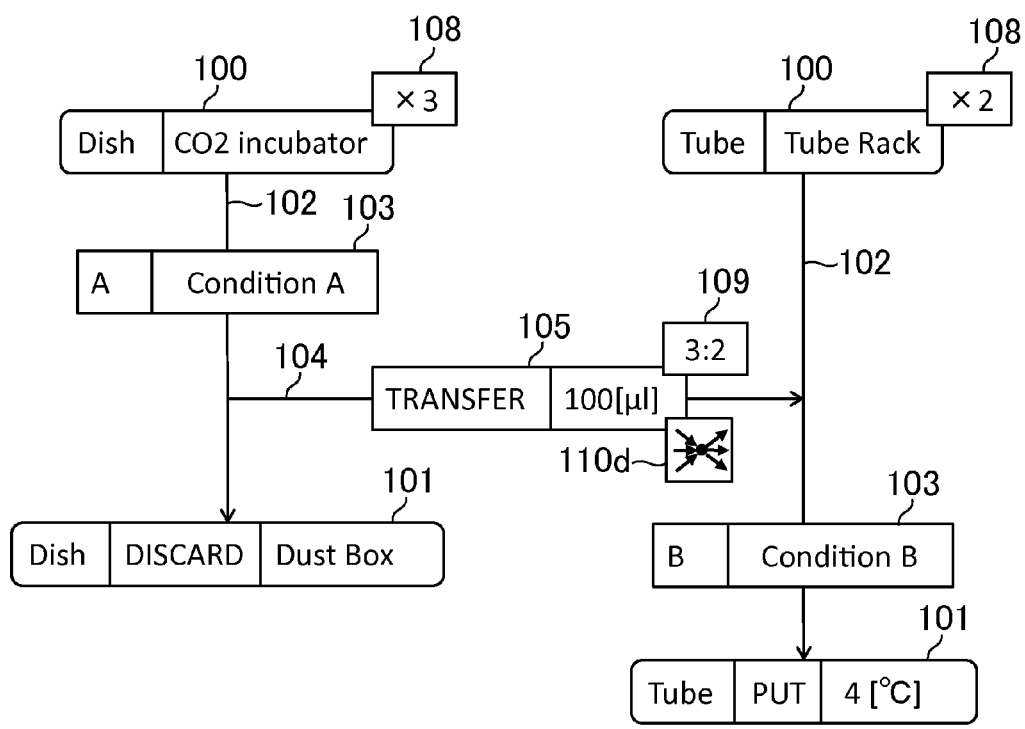
FIG. 10 is a diagram for illustrating a sixth example of the protocol chart acquired by the operation command generation device according to the embodiment of the present invention.

FIG. 10 is a diagram for illustrating a sixth example of the protocol chart acquired by the operation command generation device 1 according to this embodiment. A protocol represented by the sixth example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×3" is associated with an initial symbol 100 of "Dish" representing preparation of Petri dishes. The number-of-containers symbol 108 represents that the same process is executed for the same type of three Petri dishes. Moreover, a number-of-containers symbol 108 including characters "×2" is associated with an initial symbol 100 of "Tube" representing preparation of microtubes. The number-of-containers symbol 108 represents that the same process is executed for the same type of two microtubes.

The protocol chart of this example includes a transfer symbol 105. Moreover, a number-of-transfers symbol 109 is associated with the transfer symbol 105 representing a transfer process. The number-of-transfers symbol 109 includes the number (3) of the Petri dishes, which are the first containers, and the number (2) of the microtubes, which are the second containers. Specifically, the number-of-transfers symbol 109 includes characters "3:2", and the number of containers of a transfer source is represented on a left side of the characters, and the number of containers of a transfer destination is represented on aright side of the characters.

A fourth pictogram 110*d* is associated with the transfer symbol 105. The fourth pictogram 110*d* is a sign of three arrows extending from three points arranged on the left side of the figure toward one point at the center of the fourth pictogram 110*d* so as to converge on the one point and three arrows extending from the one point at the center toward three points arranged on the right side of the figure so as to diverge toward the three points. The number-of-transfers symbol 109 and the fourth pictogram 110*d* concisely represent a fourth transfer rule for the case in which the process subject is transferred from the three Petri dishes, which are the first containers, to the two microtubes, which are the second containers. In this example, a fourth transfer rule means a transfer rule of collecting 100 µl of the process subject from each of the first to third Petri dishes to a single intermediate container (such as beaker), and then distributing 300 µl of the process subject from the intermediate container to the first and second microtubes, which are the second containers.

The transfer rule setting unit 24 sets the fourth transfer rule when the number of the first containers is at least two, the number of the second containers is at least two, and one of those numbers is not a multiple of the other of those numbers (that is, the number of the first containers is neither a multiple nor a divisor of the number of the second containers). The transfer symbol conversion unit 23 converts, based on the fourth transfer rule, the transfer symbol 105 into a job of repeating a process of transferring the process subject from the first container to the intermediate container for all the first containers, and then repeating a process of transferring the process subject from the intermediate container to the second container for all the second containers. In this example, the number of Petri dishes, which are the first containers, is at least two, the number of the microtubes, which are the second containers, is at least two, and one of the numbers is not a multiple of the other. Thus, the transfer rule setting unit 24 sets the fourth transfer rule. Moreover, the transfer symbol conversion unit 23 converts, based on the fourth transfer rule, the transfer symbol 105 into a job of repeating, for all the Petri dishes, the process of transferring the process subject from the Petri dish to the intermediate container, and then repeating, for all the microtubes, the process of transferring the process subject from the intermediate container to the microtube. On this occasion, the intermediate container may be any container as long as the container has such a size as to contain the entire process subject contained in the plurality of Petri dishes, and may not be a single container but a plurality of containers. Moreover, as a method of distributing the process subject from the intermediate container to the plurality of microtubes, the method described in the fifth example may be employed. In other words, the distribution is the equal distribution in principle, but the ratio of the distribution may be set by the user, and the amount to be transferred from the intermediate container may be an amount smaller by a certain amount than the entire amount, such as 90% of the process subject contained in the intermediate container. In this way, with the transfer symbol conversion unit 23 and the transfer rule setting unit 24 according to this embodiment, a job of collecting the process subject to the intermediate container and distributing the process subject to a plurality of containers is generated.

Figure 11:
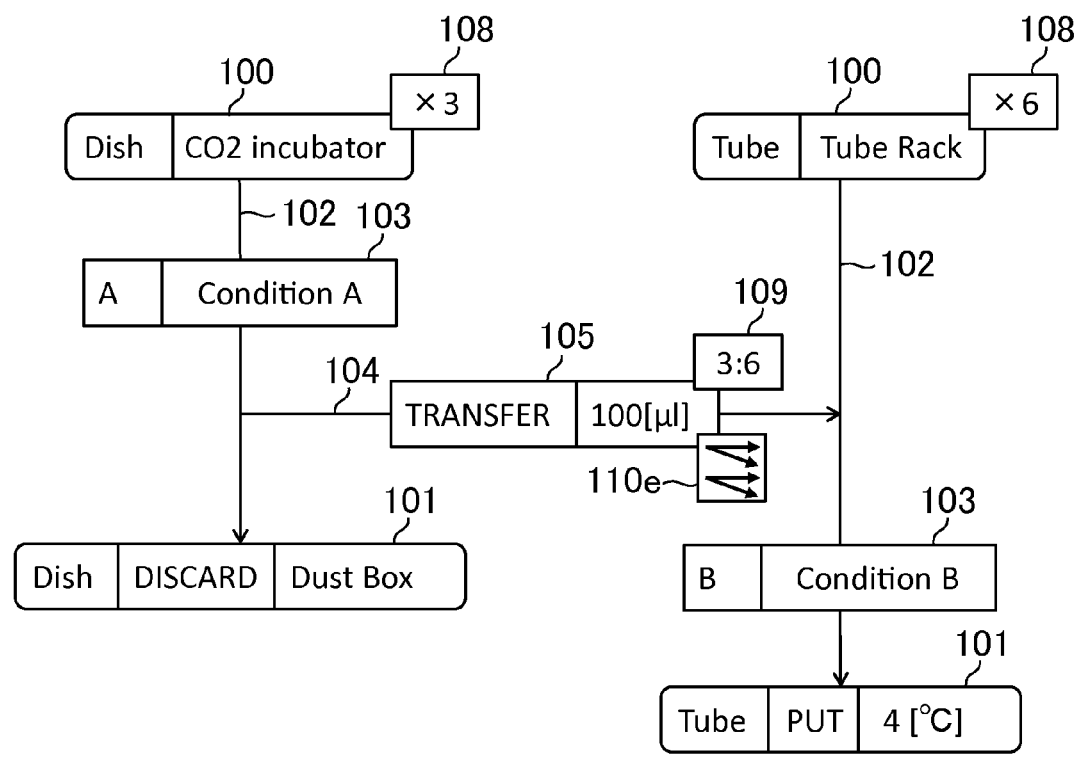
FIG. 11 is a diagram for illustrating a seventh example of the protocol chart acquired by the operation command generation device according to the embodiment of the present invention.

FIG. 11 is a diagram for illustrating a seventh example of the protocol chart acquired by the operation command generation device 1 according to this embodiment. A protocol represented by the seventh example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×3" is associated with an initial symbol 100 of "Dish" representing preparation of Petri dishes. The number-of-containers symbol 108 represents that the same process is executed for the same type of three Petri dishes. Moreover, a number-of-containers symbol 108 including characters "×6" is associated with an initial symbol 100 of "Tube" representing preparation of microtubes. The number-of-containers symbol 108 represents that the same process is executed for the same type of six microtubes.

The protocol chart of this example includes a transfer symbol 105. A number-of-transfers symbol 109 is associated with the transfer symbol 105. The number-of-transfers symbol 109 includes the number (3) of the Petri dishes, which are the first containers, and the number (6) of the microtubes, which are the second containers. Specifically, the number-of-transfers symbol 109 includes characters "3:6", and the number of containers of a transfer source is represented on a left side of the characters, and the number of containers of a transfer destination is represented on a right side of the characters.

A fifth pictogram 110e is associated with the transfer symbol 105. The fifth pictogram 110e is a sign of arrows each two of which extend from one of two points arranged on the left side of the figure toward two points out of four points arranged on the right side of the figure. The number-of-transfers symbol 109 and the fifth pictogram 110e concisely represent a fifth transfer rule for the case in which the process subject is transferred from the three Petri dishes, which are the first containers, to the six microtubes, which are the second containers. In this example, the fifth transfer rule means a transfer rule of distributing, for each of all the sets including a single Petri dish and two microtubes, 100 µl of the process subject from the single Petri dish to the two microtubes.

The transfer rule setting unit 24 sets the fifth transfer rule when the number of the first containers is at least two, the number of the second containers is at least two, and the number of the second containers is n (n: integer) times as many as the number of the first containers. The transfer symbol conversion unit 23 converts, based on the fifth transfer rule, the transfer symbol 105 into a job of repeating a process of transferring the process subject from a single first container to n second containers for all the first containers and all the second containers. In this example, the number of Petri dishes, which are the first containers, is at least two, the number of the microtubes, which are the second containers, is at least two, and the number of the microtubes is twice as many as the number of the Petri dishes. Thus, the transfer rule setting unit 24 sets the fifth transfer rule. Moreover, the transfer symbol conversion unit 23 converts, based on the fifth transfer rule, the transfer symbol 105 into a job of repeating, for all the Petri dishes and all the microtubes, the process of transferring the process subject from one Petri dish to two microtubes. As a method of distributing the process subject from each of the Petri dishes to a plurality of microtubes, the method described in the fifth example of the protocol chart may be employed. In other words, the distribution is the equal distribution in principle. Specifically, in this example, 50 µl of the process subject is distributed from the first Petri dish to each of the first and second microtubes, 50 µl of the process subject is distributed from the second Petri dish to each of the third and fourth microtubes, and 50 µl of the process subject is distributed from the third Petri dish to each of the fifth and sixth microtubes. Also in this case, the respective transfer amounts to the containers of the plurality of transfer destinations may be different from one another based on specification by the user. In this way, with the transfer symbol conversion unit 23 and the transfer rule setting unit 24 according to this embodiment, when the process subject is transferred from a plurality of containers to a plurality of containers, a plurality of jobs of each transferring the process subject from the single container to the plurality of containers are generated.

Figure 12:
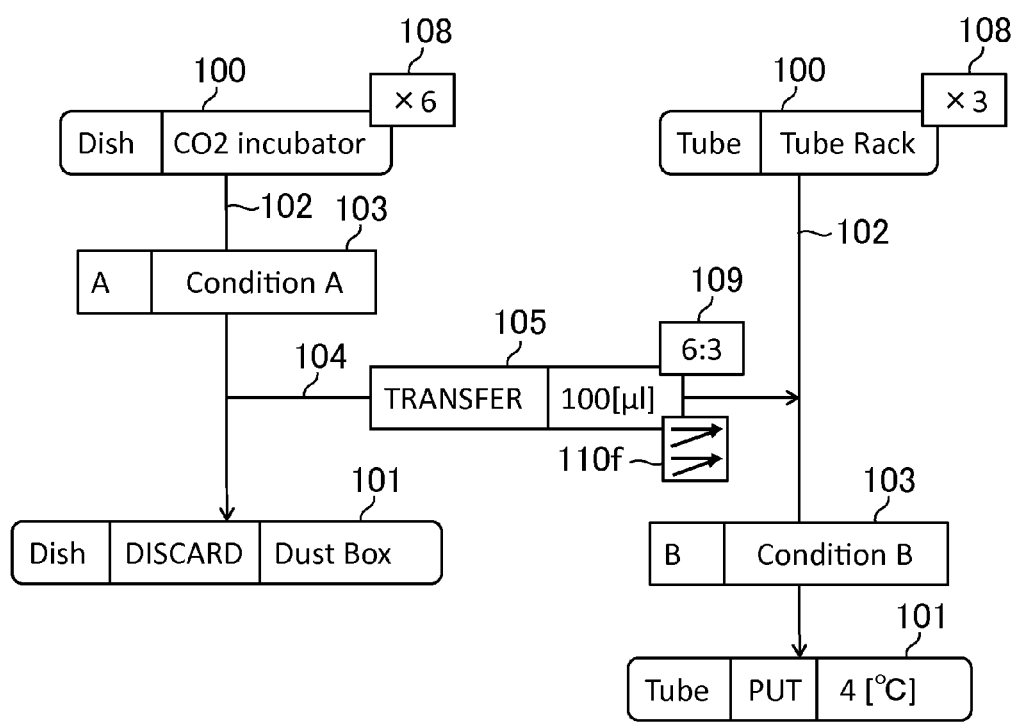
FIG. 12 is a diagram for illustrating an eighth example of the protocol chart acquired by the operation command generation device according to the embodiment of the present invention.

FIG. 12 is a diagram for illustrating an eighth example of the protocol chart acquired by the operation command generation device 1 according to this embodiment. A protocol represented by the eighth example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×6" is associated with an initial symbol 100 of "Dish" representing preparation of Petri dishes. The number-of-containers symbol 108 represents that the same process is executed for the same type of six Petri dishes. Moreover, a number-of-containers symbol 108 including characters "×3" is associated with an initial symbol 100 of "Tube" representing preparation of microtubes. The number-of-containers symbol 108 represents that the same process is executed for the same type of three microtubes.

The protocol chart of this example includes a transfer symbol 105. A number-of-transfers symbol 109 is associated with the transfer symbol 105. The number-of-transfers symbol 109 includes the number (6) of the Petri dishes, which are the first containers, and the number (3) of the microtubes, which are the second containers. Specifically, the number-of-transfers symbol 109 includes characters "6:3", and the number of containers of a transfer source is represented on a left side of the characters, and the number of containers of a transfer destination is represented on a right side of the characters.

A sixth pictogram 110*f* is associated with the transfer symbol 105. The sixth pictogram 110*f* is a sign of arrows each two of which extend from two points out of four points arranged on the left side of the figure toward one of two points arranged on the right side of the figure. The number-of-transfers symbol 109 and the sixth pictogram 110*f* concisely represent a sixth transfer rule for the case in which the process subject is transferred from the six Petri dishes, which are the first containers, to the three microtubes, which are the second containers. In this example, the sixth transfer rule means a transfer rule of collecting, for each of all the sets including two Petri dishes and a single microtube, 100 µl of the process subject from the two Petri dishes to the single microtube.

The transfer rule setting unit 24 sets the sixth transfer rule when the number of the first containers is at least two, the number of the second containers is at least two, and the number of the first containers is n (n: integer) times as many as the number of the second containers. The transfer symbol conversion unit 23 converts, based on the sixth transfer rule, the transfer symbol 105 into a job of repeating a process of transferring the process subject from n first containers to a single second container for all the first containers and all the second containers. In this example, the number of Petri dishes, which are the first containers, is at least two, the number of the microtubes, which are the second containers, is at least two, and the number of the Petri dishes is twice as many as the number of the microtubes. Thus, the transfer rule setting unit 24 sets the sixth transfer rule. Moreover, the transfer symbol conversion unit 23 converts, based on the sixth transfer rule, the transfer symbol 105 into a job of repeating, for all the Petri dishes and all the microtubes, the process of transferring the process subject from two Petri dishes to one microtube. Specifically, in this example, 100 µl of the process subject is transferred from each of the first and second Petri dishes to the first microtube, 100 µl of the process subject is transferred from each of the third and fourth Petri dishes to the second microtube, and 100 µl of the process subject is transferred from each of the fifth and sixth Petri dishes to the third microtube. As a result, each of the three microtubes contains 200 µl of the process subject. In this way, with the transfer symbol conversion unit 23 and the transfer rule setting unit 24 according to this embodiment, when the process subject is transferred from a plurality of containers to a plurality of containers, a plurality of jobs of each transferring the process subject from the plurality of containers to the single container are generated.

Figure 13:
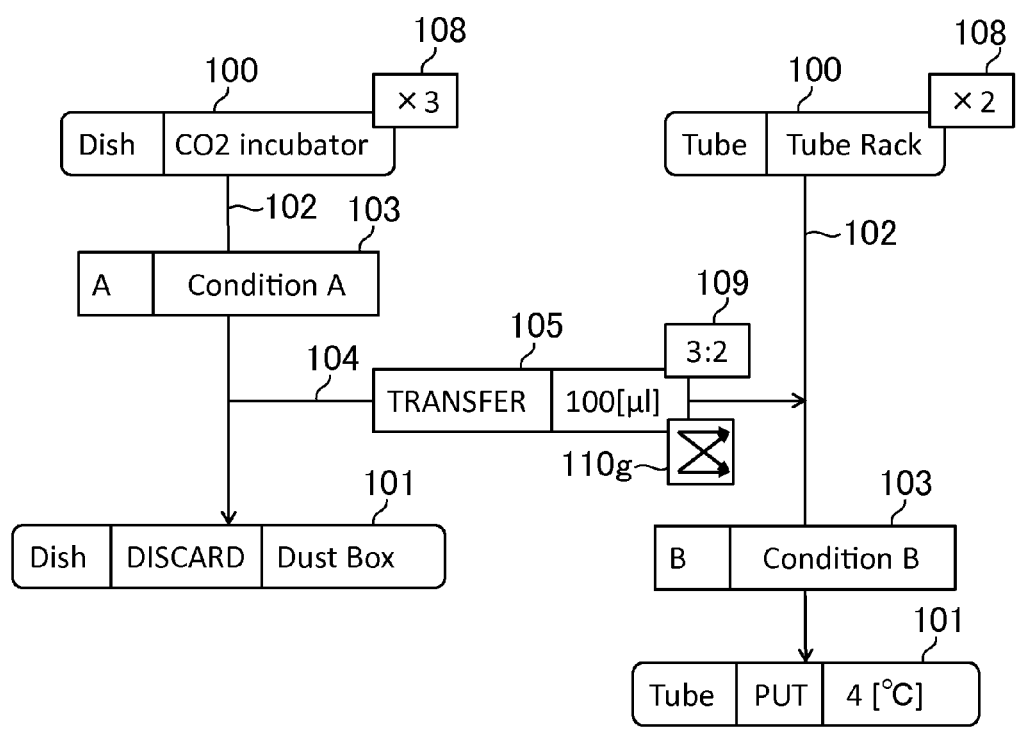
FIG. 13 is a diagram for illustrating a ninth example of the protocol chart acquired by the operation command generation device according to the embodiment of the present invention.

FIG. 13 is a diagram for illustrating a ninth example of the protocol chart acquired by the operation command generation device 1 according to this embodiment. A protocol represented by the ninth example represents that, after Process A is executed for a Petri dish, which is the first container, 100 µl of a content is transferred to a microtube, which is the second container, the Petri dish is discarded, Process B is executed for the microtube, and the microtube is kept in the thermostatic bath at 4° C. On this occasion, a number-of-containers symbol 108 including characters "×3" is associated with an initial symbol 100 of "Dish" representing preparation of Petri dishes. The number-of-containers symbol 108 represents that the same process is executed for the same type of three Petri dishes. Moreover, a number-of-containers symbol 108 including characters "×2" is associated with an initial symbol 100 of "Tube" representing preparation of microtubes. The number-of-containers symbol 108 represents that the same process is executed for the same type of two microtubes.

The protocol chart of this example includes a transfer symbol 105. A number-of-transfers symbol 109 is associated with the transfer symbol 105. The number-of-transfers symbol 109 includes the number (3) of the Petri dishes, which are the first containers, and the number (2) of the microtubes, which are the second containers. Specifically, the number-of-transfers symbol 109 includes characters "3:2", and the number of containers of a transfer source is represented on a left side of the characters, and the number of containers of a transfer destination is represented on a right side of the characters.

A seventh pictogram 110*g* is associated with the transfer symbol 105. The seventh pictogram 110*g* is a sign of four arrows each extending from one of two points arranged on the left side of the figure toward two points arranged on the right side of the figure. The number-of-transfers symbol 109 and the seventh pictogram 110*g* mean a transfer rule of distributing 100 µl of the process subject from each of the first to third Petri dishes to the first and second microtubes, which are the second containers.

The transfer rule setting unit 24 sets a seventh transfer rule when the number of the first containers is at least two, the number of the second containers is at least two, and, for example, application of the seventh transfer rule is explicitly represented on the protocol chart, or such a setting is made in advance that the seventh transfer rule is to be applied preferentially over the first to sixth transfer rules. According to this embodiment, the transfer rule setting unit 24 preferentially applies the seventh transfer rule over the first to sixth transfer rules, and hence, as described in this case, applies the seventh transfer rule described below based on a state in which the application of the seventh transfer rule is explicitly represented by the seventh pictogram 110*g*. In contrast, the transfer rule setting unit 24 may be configured to apply the seventh transfer rule preferentially, or may permit the selection of the priorities of the transfer rules to be applied in response to the setting by the user.

In this example, the application of the seventh transfer rule is explicitly represented by the seventh pictogram 110g, and the transfer symbol conversion unit 23 thus converts, based on the seventh transfer rule, the transfer symbol 105 into a job of repeating the process of transferring the process subject from a single first container to all the second containers for all the first containers. In this example, the transfer symbol conversion unit 23, based on the seventh transfer rule, converts the transfer symbol 105 into a job of repeating the process of transferring the process subject from one Petri dish to all the microtubes for all the Petri dishes. As a method of distributing the process subject from each of the Petri dishes to the plurality of microtubes, the method described in the fifth example of the protocol chart may be employed. In other words, the distribution is the equal distribution in principle. Specifically, in this example, 50 µl of the process subject may be transferred from the first Petri dish to each of the first and second microtubes, 50 µl of the process subject may be transferred from the second Petri dish to each of the first and second microtubes, and 50 µl of the process subject may be transferred from the third Petri dish to each of the first and second microtubes. As a result, each of the microtubes contains 150 µl of the process subject. Moreover, such a point that the respective transfer amounts to the containers of the plurality of destinations may be different from each other based on specification by the user and the like are the same as those in the examples described above. In this way, with the transfer symbol conversion unit 23 and the transfer rule setting unit 24 according to this embodiment, a job of transferring the process subject respectively from a plurality of containers to a plurality of containers is generated.

Figure 14:
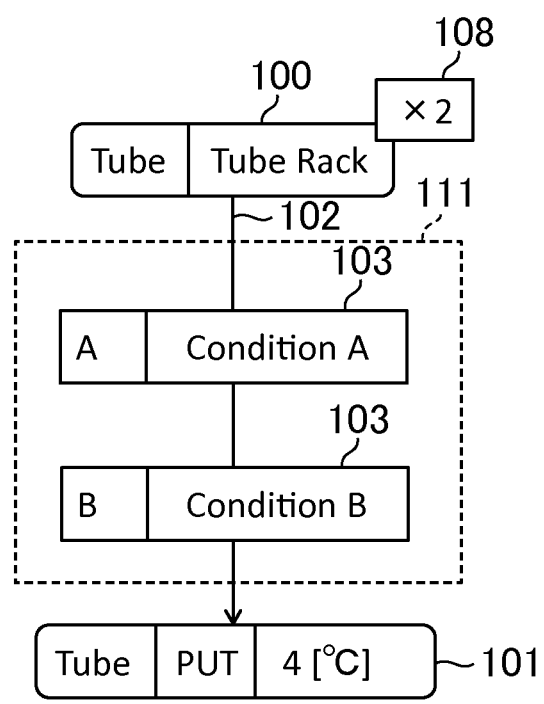
FIG. 14 is a diagram for illustrating a tenth example of the protocol chart acquired by the operation command generation device according to the embodiment of the present invention.

FIG. 14 is a diagram for illustrating a tenth example of the protocol chart acquired by the operation command generation device according to the embodiment of the present invention. The protocol chart of the tenth example represents a protocol of executing Process A and Process B for two microtubes, and then respectively storing the two microtubes in the thermostatic baths at 4° C.

In this example, a consecutive process symbol 111 is arranged so as to be associated with two process symbols 103 representing Processes A and B. The consecutive process symbol 111 is represented by a frame line formed by broken lines, and association between the process symbols 103 and the consecutive process symbol 111 is explicitly represented by enclosing the two process symbols 103 representing Processes A and B with the frame line. The consecutive process symbol 111 encloses the process symbols 103 to be consecutively executed with the frame line, to thereby explicitly represent that the process symbols 103 are to be consecutively executed for a single container (in this example, a single microtube).

In this example, the number-of-containers symbol 108 is arranged so as to be associated with an initial symbol 100. The number-of-containers symbol 108 of this example includes characters "×2", and explicitly represents that the initial symbol 100 corresponds to two containers. The number-of-containers extraction unit 14 extracts two, which is the number of the containers associated with the initial symbol 100. The process symbol conversion unit 16 converts process symbols representing Processes A and B into jobs of Processes A and B to be executed for each of the two microtubes.

The execution order of the jobs is defined while two sets including the initial symbol 100 in which "Tube" is written, a final symbol 101, and a procedure line 102 connecting the both symbols to each other are considered to be arranged as being separated from each other in the second direction and arranged at the same position in the first direction. On this occasion, the consecutive process setting unit 19 makes such a setting that processes represented by the plurality of process symbols with which the consecutive process symbol 111 is associated are to be consecutively executed. The process symbol conversion unit 16 receives this setting, to thereby convert the plurality of symbols into jobs to be consecutively executed for a single container. In this example, the consecutive process setting unit 19 makes such a setting as consecutively executing Processes A and B for the first microtube and consecutively executing Processes A and B for the second microtube. Moreover, the process symbol conversion unit 16 converts the two process symbols representing Processes A and B into jobs of executing Processes A and B consecutively for the first microtube, and then executing Processes A and B consecutively for the second microtube. In this way, with the consecutive process setting unit 19 according to this embodiment, jobs to be consecutively executed for a single container are generated.

Figure 15:
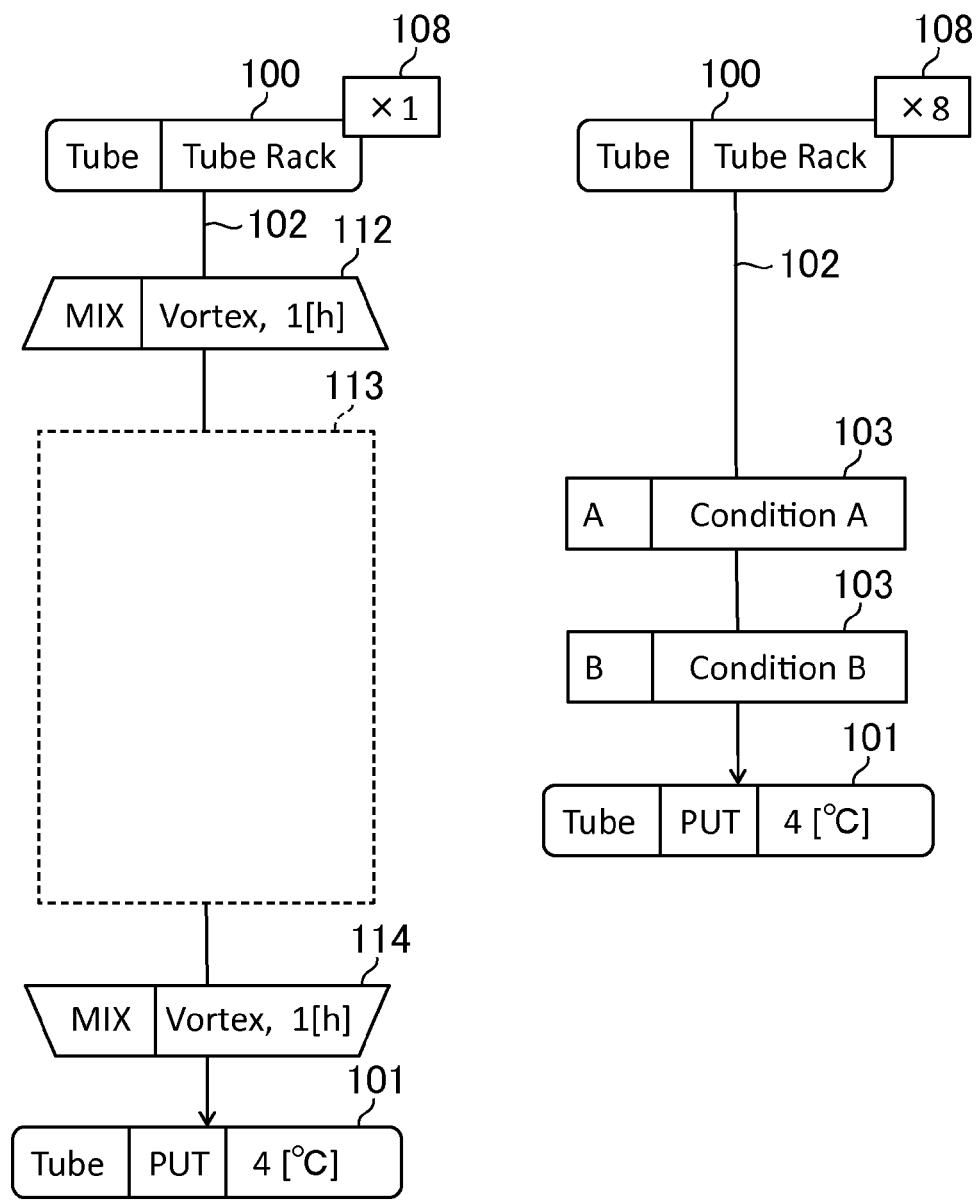
FIG. 15 is a diagram for illustrating an eleventh example of the protocol chart acquired by the operation command generation device according to the embodiment of the present invention.

FIG. 15 is a diagram for illustrating an eleventh example of the protocol chart acquired by the operation command generation device 1 according to the embodiment of the present invention. The protocol chart of the eleventh example represents a protocol of executing an agitation process (process represented as "MIX") for a single microtube, and, simultaneously in parallel with the agitation process, executing Processes A and B and a storage process of storing the microtube in the thermostatic bath at 4° C. for each of eight microtubes, which are other containers.

In this example, a parallel process symbol is arranged so as to be associated with the process symbols 103 representing Processes A and B for the eight microtubes. The parallel process symbol includes a parallel process start point symbol 112, a parallel process section symbol 113, and a parallel process end point symbol 114. The parallel process start point symbol 112 represents a start point of a section in which the agitation process, which is a second process, and Processes A and B, which are first processes, are to be executed simultaneously in parallel. The parallel process start point symbol 112 represents that the second process is the agitation process to be executed for one hour by using the agitator ("Vortex, 1 [h]"). The parallel process start point symbol 112 is arranged so as to be separated toward the initial symbol 100 side with respect to the process symbol 103 of Process A in the first direction. With this arrangement, the parallel process start point symbol 112 explicitly represents a start point of the section in which the parallel process is to be executed.

The parallel process section symbol 113 represents the section in which the first processes and the second process are to be executed simultaneously in parallel in the first direction. In this example, the parallel process section symbol 113 is represented by a frame line formed by broken lines, and occupies a certain range in the first direction. The process symbol 103 of Process A, the process symbol 103 of Process B, and the final symbol 101 for the eight microtubes are arranged so as to be separated from the parallel process section symbol 113 in the second direction in the range occupied by the parallel process section symbol 113 in the first direction. With this arrangement, Processes A and B and the storage process are explicitly represented as the parallel processes to be executed simultaneously in parallel with the agitation process.

The parallel process end point symbol 114 represents an end point of the section in which the agitation process, which is the second process, and Processes A and B, which are the first processes, are to be executed simultaneously in parallel. The parallel process endpoint symbol 114 represents that the second process is the agitation process to be executed for one hour by using the agitator ("Vortex, 1 [h]"). The parallel process end point symbol 114 is arranged so as to be separated on a final symbol 101 side for the single microtube with respect to the final symbol 101 representing the storage process for the eight microtubes. With this arrangement, the parallel process end point symbol 114 explicitly represents an endpoint of the section in which the parallel process is to be executed.

The parallel process setting unit 18 makes such a setting that the first processes represented by the process symbol with which the parallel process symbol is associated and the second process are to be executed simultaneously in parallel. The process symbol conversion unit 16 converts, based on the setting by the parallel process setting unit 18, the process symbols into jobs to be executed simultaneously in parallel with the second process. In this example, the parallel process setting unit 18 makes such a setting that Processes A and B represented by the process symbols 103 with which the parallel process symbol is associated and the agitation process are to be executed simultaneously in parallel. Moreover, the process symbol conversion unit 16 converts the process symbols 103 representing Processes A and B into jobs of Processes A and B for the eight microtubes to be executed simultaneously with the agitation process based on the setting by the parallel process setting unit 18. Moreover, in this example, the final symbol conversion unit 15 converts the final symbol 101 for the eight microtubes into a job of storing the eight microtubes in the thermostatic bath at 4° C. simultaneously in parallel with the agitation process executed by the agitator 8 for the single microtube. In this way, with the parallel process setting unit 18 according to this embodiment, jobs to be executed simultaneously in parallel with each other are generated.

Figure 16:
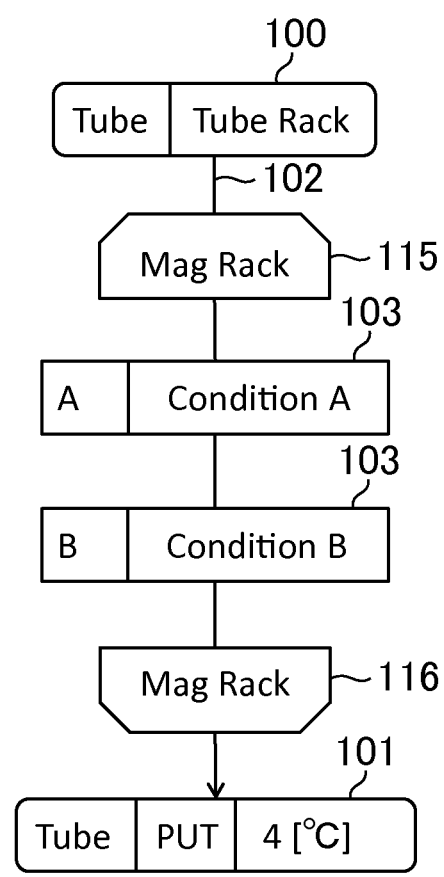
FIG. 16 is a diagram for illustrating a twelfth example of the protocol chart acquired by the operation command generation device according to the embodiment of the present invention.

FIG. 16 is a diagram for illustrating a twelfth example of the protocol chart acquired by the operation command generation device 1 according to the embodiment of the present invention. The protocol chart of the twelfth example represents a protocol of executing Processes A and B for a single microtube on a magnet rack ("Mag Rack"), and then storing the microtube in the thermostatic bath at 4° C. A magnetic force acts on a container placed on the magnet rack in a certain direction, and a content of the container is separated into components attracted by the magnetic force and components not attracted by the magnetic force. When a process is executed while a content of the container is separated into a plurality of components, the magnet rack is selected as a place for executing the process.

An area symbol includes an area start point symbol 115 and an area endpoint symbol 116. The area symbol represents an area in which processes for a container is to be executed, and is arranged so as to be associated with process symbols 103 representing the processes. In this example, the area start point symbol 115 and the area end point symbol 116 represent the magnet rack, which is the area in which the processes for the container are to be executed, by using the characters "Mag Rack". In this example, the area start point symbol 115 and the area end point symbol 116 are arranged on both sides of the process symbols 103 for Processes A and B, which are process symbols for which the work area is specified, in the first direction. With this arrangement, the association between the area symbol and the process symbols are explicitly represented, and the processes to be executed in a specific area are explicitly represented.

The work area setting unit 20 sets a work area in which processes represented by process symbols with which an area symbol is associated are to be executed. The process symbol conversion unit 16 converts the process symbols into jobs to be executed in the work area set by the work area setting unit 20 based on the setting by the work area setting unit 20. In this example, the work area setting unit 20 sets the magnet rack as the work area in which Processes A and B represented by the process symbols 103 with which the area symbol is associated are to be executed. Moreover, the process symbol conversion unit 16 converts the process symbols 103 representing Processes A and B into the jobs of Processes A and B to be executed on the magnet rack based on the setting by the work area setting unit 20. In this way, the work area setting unit 20 according to this embodiment sets a work area in which jobs are to be executed.

The operation command generated by the operation command generation unit 12 as described above is provided to the robot controller 2. The robot controller 2 rewrites the operation command into data which can be read by the robot 3 depending on necessity, to thereby control the operation of the robot 3. The robot 3 executes the protocol represented by the protocol chart under the control of the robot controller 2. On this occasion, in some cases, before the protocol is actually executed, a time required for execution of the protocol needs to be acquired, to thereby check the time required for the execution of the protocol in advance. The operation command generation device 1 according to this embodiment uses the execution time calculation unit 25 to calculate the time required for execution of jobs generated based on the protocol chart. The execution time calculation unit 25 simulates the operation of the robot 3, to thereby calculate the time required for execution of the protocol. Moreover, the execution time calculation unit 25 may define a standard execution time for each job, and refer to the standard execution times of respective jobs acquired by converting respective elements on the protocol chart, to thereby calculate a time required for all the jobs.

Figure 17:
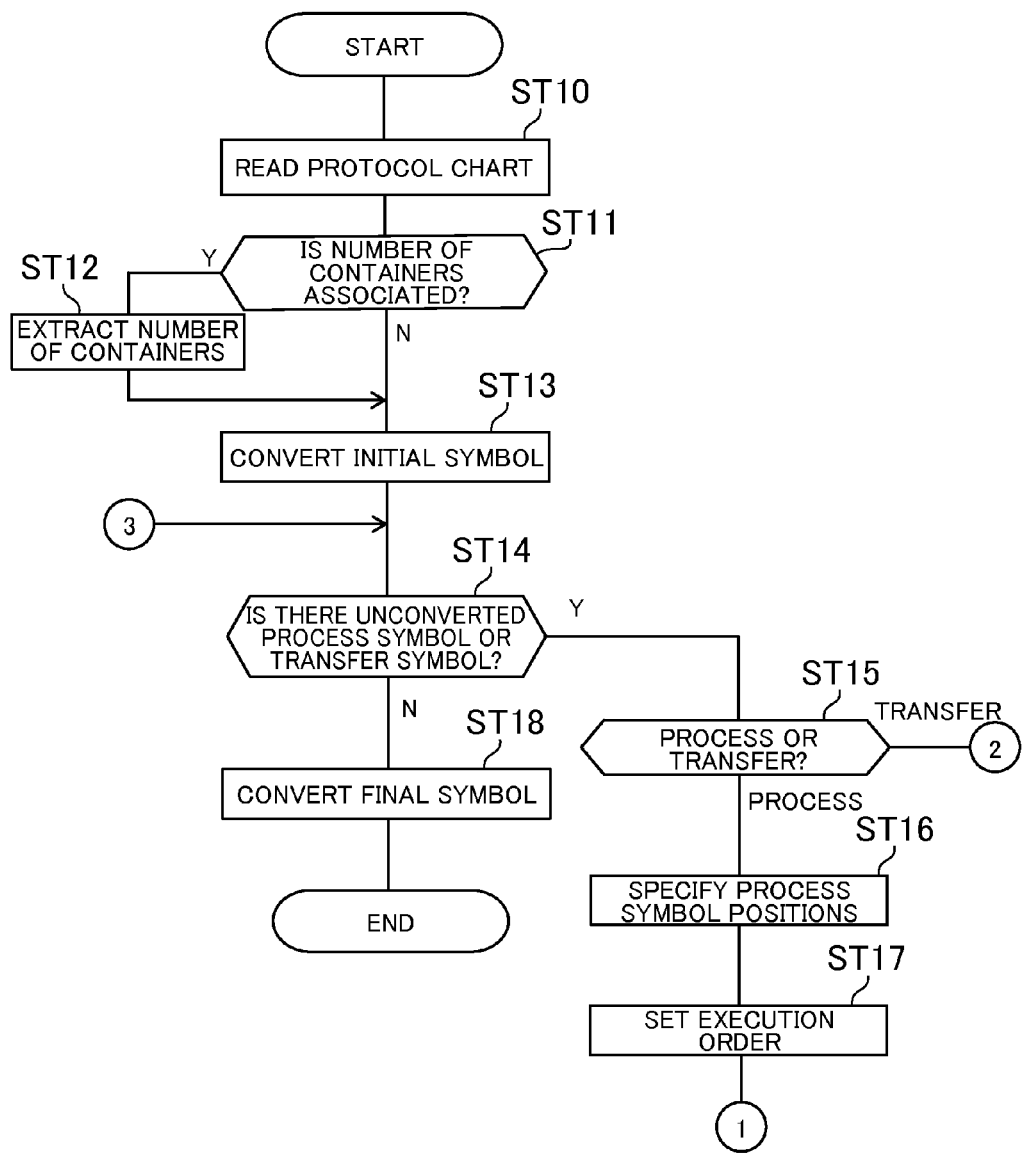
FIG. 17 is a first flowchart for illustrating operations of an operation command generation unit according to the embodiment of the present invention.

FIG. 17 is a first flowchart for illustrating operations of the operation command generation unit 12 according to this embodiment.

First, in Step ST10, the operation command generation unit reads a protocol chart acquired by the protocol chart acquisition unit 11. Then, in Step ST11, whether the number of containers is associated with an initial symbol described in the read protocol chart or not is determined. Whether the number of containers is associated with the initial symbol or not may be determined based on absence/presence of a number-of-containers symbol, or by reading a parameter accompanying the initial symbol.

When the number of containers is associated with the initial symbol, in Step ST12, the number-of-containers extraction unit 14 extracts the number of containers associated with the initial symbol. Then, in Step ST13, the initial symbol conversion unit 13 converts the initial symbol described on the protocol chart into a job of preparing the containers for containing a process subject.

Then, in Step ST14, whether or not a process symbol or a transfer symbol that has not been converted into a job exists on the protocol chart is determined. When an unconverted process symbol or transfer symbol exists, in Step ST15, whether the unconverted symbol is a process symbol or a transfer symbol is determined. When the unconverted symbol is a transfer symbol, the operation command generation unit 12 proceeds to processing illustrated in FIG. 19.

On the other hand, when the unconverted symbol is a process symbol, the operation command generation unit proceeds to Step ST16, and the process symbol position specification unit 22 specifies at least two process symbols equal to each other in the arrangement position in the first direction. Then, in Step ST17, the execution order determination unit 21 determines an execution order of a plurality of process symbols based on respective arrangement positions of the plurality of process symbols on the protocol chart. On this occasion, when at least two process symbols are specified by the process symbol position specification unit 22, the execution order determination unit 21 determines an execution order of the specified at least two process symbols based on the arrangement positions in the second direction. Then, the operation command generation unit 12 proceeds to processing described in a next flowchart.

In Step ST14, when it is determined that a process symbol or a transfer symbol that has not been converted into a job does not exist on the protocol chart, in Step ST18, the final symbol conversion unit 15 converts a final symbol into a job of executing a final process for the container. Then, the generation of the operation command by the operation command generation unit 12 is finished.

Figure 18:
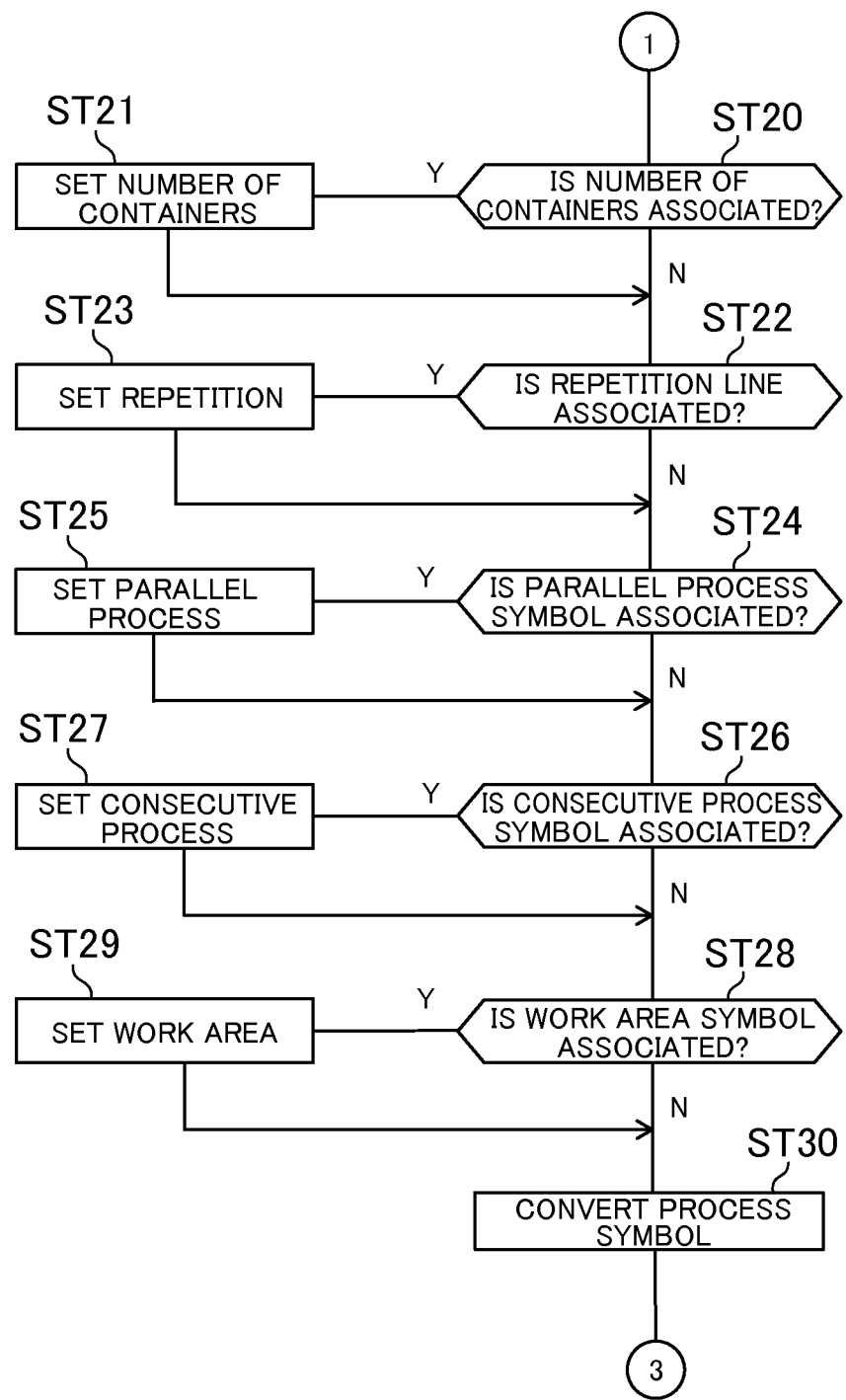
FIG. 18 is a second flowchart for illustrating operations of the operation command generation unit according to the embodiment of the present invention.

FIG. 18 is a second flowchart for illustrating operations of the operation command generation unit 12 according to this embodiment. The second flowchart is an illustration of a series of processes executed after the execution order of the process symbols is determined in Steps ST15 to ST17 illustrated in FIG. 17.

First, in Step ST20, the operation command generation unit 12 determines whether the number of containers associated with the initial symbol has been extracted by the number-of-containers extraction unit 14 or not. When the number of the containers has been extracted, in Step ST21, the process symbol conversion unit 16 makes such a setting that a process symbol associated with the initial symbol is converted into as many jobs as the extracted number of containers.

Then, in Step ST22, the operation command generation unit 12 determines whether a process symbol with which a repetition line is associated exists or not. When a process symbols with which a repetition line is associated exists, in Step ST23, the repetition setting unit 17 sets the number of repetitions of the process symbol with which the repetition line is associated.

Then, in Step ST24, the operation command generation unit 12 determines whether a process symbol with which a parallel process symbol is associated exists or not. When a process symbol with which a parallel process symbol is associated exists, in Step ST25, the parallel process setting unit 18 makes such a setting that a first process represented by the process symbol with which the parallel process symbol is associated and a second process are to be executed simultaneously in parallel.

Then, in Step ST26, the operation command generation unit 12 determines whether a plurality of process symbols with which a consecutive process symbol is associated exist or not. When a plurality of process symbols with which a consecutive process symbol is associated exist, in Step ST27, the consecutive process setting unit 19 makes such a setting that processes represented by the plurality of process symbols with which the consecutive process symbol is associated are to be consecutively executed.

Further, in Step ST28, the operation command generation unit 12 determines whether a process symbol with which an area symbol is associated exists or not. When a process symbol with which an area symbol is associated exists, in Step ST29, the work area setting unit 20 sets a work area in which a process represented by the process symbol with which the area symbol is associated is to be executed.

Finally, in Step ST30, the process symbol conversion unit 16 converts the process symbol into a job based on the setting of the number of containers, the setting of the repetition process by the repetition setting unit 17, the setting of the parallel process by the parallel process setting unit 18, the setting of the consecutive process by the consecutive process setting unit 19, and the setting of the work area by the work area setting unit 20. Then, the operation command generation unit 12 returns to Step ST14, and continues the conversion until an unconverted process symbol or transfer symbol no longer exists.

Figure 19:
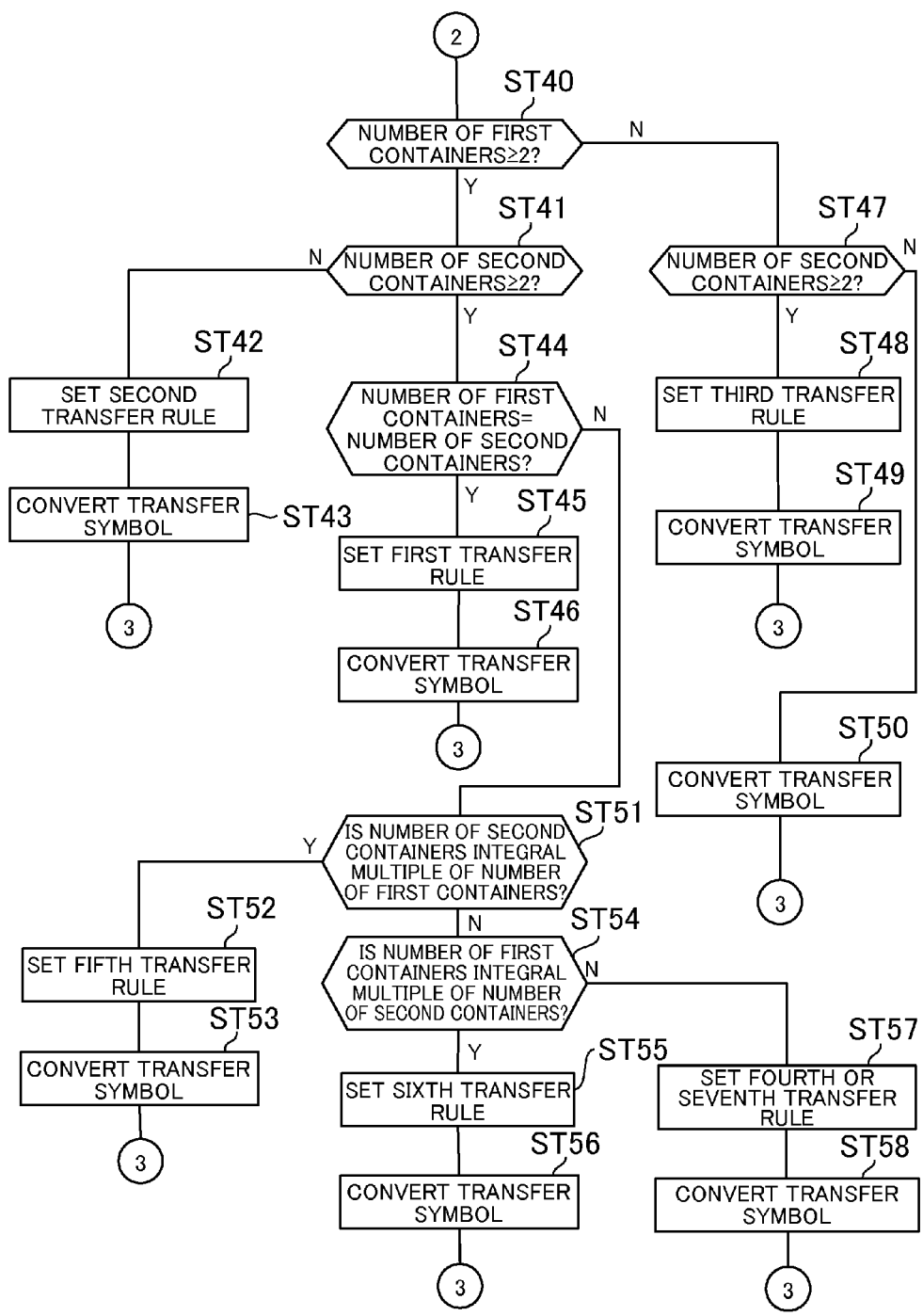
FIG. 19 is a third flowchart for illustrating operations of the operation command generation unit according to the embodiment of the present invention.
}

FIG. 19 is a third flowchart for illustrating operations of the operation command generation unit 12 according to this embodiment. The third flowchart is an illustration of a series of processes executed when the unconverted symbol is determined to be a transfer symbol in Step ST15 of FIG. 17.

First, in Step ST40, the operation command generation unit 12 determines whether the number of first containers, which are containers of a transfer source, is at least two or not. When the number of the first containers is at least two, in Step ST41, whether the number of second containers, which are containers of a transfer destination, is at least two or not is determined.

When the number of the first containers is at least two, and the number of the second containers is not at least two, that is, the number of the first containers is at least two, and the number of the second containers is one, in Step ST42, the transfer rule setting unit 24 sets the second transfer rule. Then, in Step ST43, the transfer symbol conversion unit 23 converts, based on the second transfer rule, the transfer symbol into a job of repeating the process of transferring the process subject from the first container to the second container for all the first containers. Then, the operation command generation unit 12 returns to Step ST14, and continues the conversion until an unconverted process symbol or transfer symbol no longer exists.

On the other hand, when the number of the first containers is at least two, and the number of the second containers is at least two, in Step ST44, the operation command generation unit 12 determines whether the number of the first containers and the number of the second containers are equal to each other or not. When the number of the first containers and the number of the second containers are equal to each other, in Step ST45, the transfer rule setting unit 24 sets the first transfer rule. Then, in Step ST46, the transfer symbol conversion unit 23 converts, based on the first transfer rule, the transfer symbol into a job of repeating the process of transferring the process subject from the first container to the second container in a one-to-one manner as many times as the number of the containers. Then, the operation command generation unit 12 returns to Step ST14, and continues the conversion until an unconverted process symbol or transfer symbol no longer exists.

Moreover, in Step ST40, when the number of the first containers is determined not to be at least two, in Step ST47, whether the number of the second containers is at least two or not is determined. Then, when the number of the second containers is determined to be at least two, that is, the number of the first containers is one, and the number of the second containers is at least two, in Step ST48, the transfer rule setting unit 24 sets the third transfer rule. Then, in Step ST49, the transfer symbol conversion unit 23 converts, based on the third transfer rule, the transfer symbol into a job of repeating the process of transferring the process subject from the first container to the second container for all the second containers. Then, the operation command generation unit 12 returns to Step ST14, and continues the conversion until an unconverted process symbol or transfer symbol no longer exists.

On the other hand, in Step ST47, when the number of the second containers is determined not to be at least two, that is, the number of the first containers is one, and the number of the second containers is one, in Step ST50, the transfer symbol conversion unit 23 converts the transfer symbol into a job of transferring the process subject from the first container to the second container. Then, the operation command generation unit 12 returns to Step ST14, and continues the conversion until an unconverted process symbol or transfer symbol no longer exists.

Further, in Step ST44, when the number of the first containers and the number of the second containers are determined not to be equal to each other, in Step ST51, whether the number of the second container is an integral multiple of the number of the first containers or not is determined. When the number of the second containers is determined to be an integral multiple of the number of the first containers, that is, the number of the first containers is at least two, the number of the second containers is at least two, and the number of the second containers is an integral multiple of the number of the first containers, in Step ST52, the transfer rule setting unit 24 sets the fifth transfer rule. Then, the transfer symbol conversion unit 23 converts, based on the fifth transfer rule, the transfer symbol into a job of repeating the process of transferring the process subject from a single first container to as many second containers as the integer for all the first containers without an overlap in terms of the second container. Then, the operation command generation unit 12 returns to Step ST14, and continues the conversion until an unconverted process symbol or transfer symbol no longer exists.

In Step ST51, when the number of the second containers is determined not to be an integral multiple of the number of the first containers, in Step ST54, whether the number of the first containers is an integral multiple of the number of the second containers or not is determined. When the number of the first containers is determined to bean integral multiple of the number of the second containers, that is, the number of the first containers is at least two, the number of the second containers is at least two, and the number of the first containers is an integral multiple of the number of the second containers, in Step ST55, the transfer rule setting unit 24 sets the sixth transfer rule. Then, the transfer symbol conversion unit 23 converts, based on the sixth transfer rule, the transfer symbol into a job of repeating the process of transferring the process subject from as many first containers as the integer to a single second container for all the second containers without an overlap in terms of the first container. Then, the operation command generation unit 12 returns to Step ST14, and continues the conversion until an unconverted process symbol or transfer symbol no longer exists.

When, in Step ST54, the number of the first containers is determined not to be an integral multiple of the number of the second containers, that is, the number of the first containers is at least two, and the number of the second containers is at least two, in Step ST57, the transfer rule setting unit 24 sets the fourth transfer rule or the seventh transfer rule. On this occasion, which of the transfer rules is set is defined based on a command from the user of the operation command generation device 1. Note that, also in Steps ST52 and ST55, the fourth transfer rule or the seventh transfer rule may be set based on a command from the user.

When the fourth transfer rule is set in Step ST57, in Step ST58, the transfer symbol conversion unit 23 converts, based on the fourth transfer rule, the transfer symbol into a job of repeating the process of transferring the process subject from the first container to the intermediate container for all the first containers, and then repeating the process of transferring the process subject from the intermediate container to the second container for all the second containers. On the other hand, when the seventh transfer rule is set in Step ST57, in Step ST58, the transfer symbol conversion unit 23 converts, based on the seventh transfer rule, the transfer symbol into a job of repeating the process of transferring the process subject from a single first container to all the second containers for all the first containers. Then, the operation command generation unit 12 returns to Step ST14, and continues the conversion until an unconverted process symbol or transfer symbol no longer exists.

Each of the configurations in the embodiment above is described as a specific example, and the invention disclosed in this specification is not intended to be limited to those specific configurations themselves. Various modifications may be made by a person skilled in the art to the disclosed embodiment. For example, the functions, the operation method, and the like may be appropriately changed and added. Further, the control illustrated in the first to third flowcharts may also be appropriately replaced by one having the same functions. It is intended that the technical scope of the invention disclosed in this specification cover all such modifications. It should be understood by those skilled in the art that various modifications, combinations, sub-combinations and alterations may occur depending on design requirements and other factors insofar as they are within the scope of the appended claims or the equivalents thereof.

What is claimed is:

1. An operation command generation device, comprising:
    an execution order determination unit configured to determine, based on respective arrangement positions of a plurality of process symbols each representing a process for a process subject on a protocol chart comprising the plurality of process symbols, an execution order of the plurality of process symbols; and
    a process symbol conversion unit configured to respectively convert the plurality of process symbols into jobs for a process system comprising at least a robot so that processes represented by the plurality of process symbols are executed in the execution order determined by the execution order determination unit;
    wherein the protocol chart further comprises an initial symbol with which at least one process symbol is associated, the initial symbol representing a container for the process subject,
    wherein some of the process symbols are arranged along a first direction from the initial symbol,
    wherein another initial symbol is arranged being separate from the initial symbol in a second direction intersecting the first direction, and the former initial symbol and the latter initial symbol represent different containers, and
    wherein the execution order of the processes represented by the process symbols arranged at equal position in the first direction is determined according to their position in the second direction.

2. The operation command generation device according to claim 1,
    wherein the operation command generation device further comprises an initial symbol conversion unit configured to convert the initial symbol into a job of preparing the container for containing the process subject.

3. The operation command generation device according to claim 1,
wherein the protocol chart further comprises an initial symbol with which at least one process symbol is associated, the initial symbol representing a container for the process subject,
wherein the operation command generation device further comprises a number-of-containers extraction unit configured to extract a number of containers associated with the initial symbol based on the protocol chart, and
wherein the process symbol conversion unit is further configured to convert the process symbol associated with the initial symbol into as many jobs as the number of containers extracted by the number-of-containers extraction unit.

4. The operation command generation device according to claim 1,
wherein the protocol chart further comprises a parallel process symbol arranged so as to be associated with a process symbol,
wherein the operation command generation device further comprises a parallel process setting unit configured to make such a setting that a first process represented by the process symbol and a second process are to be simultaneously executed in parallel, and
wherein the process symbol conversion unit is further configured to convert, based on the setting by the parallel process setting unit, the process symbol into a job to be simultaneously executed in parallel with the second process.

5. The operation command generation device according to claim 1,
wherein the protocol chart further comprises an area symbol arranged so as to be associated with the process symbol,
wherein the operation command generation device further comprises a work area setting unit configured to set a work area in which the process represented by the process symbol is to be executed, and
wherein the process symbol conversion unit is further configured to convert, based on the setting by the work area setting unit, the process symbol into a job to be executed in the work area.

6. The operation command generation device according to claim 1,
wherein the protocol chart further comprises a repetition line arranged so as to be associated with the process symbol,
wherein the operation command generation device further comprises a repetition setting unit configured to set a number of repetitions of the process symbol, and
wherein the process symbol conversion unit is further configured to convert the process symbol into a job to be repeated as many times as the number of repetitions.

7. The operation command generation device according to claim 1,
wherein the protocol chart further comprises a final symbol representing a final state of the container, and
wherein the operation command generation device further comprises a final symbol conversion unit configured to convert the final symbol into a job of executing a final process for the container.

8. The operation command generation device according to claim 1, further comprising an execution time calculation unit configured to calculate a time required for execution of the job generated based on the protocol chart.

9. A non-transitory computer-readable storage medium storing a computer program for causing a computer to function as the operation command generation device of claim 1.

10. The operation command generation device according to claim 1, further comprising a process symbol position specification unit configured to specify at least two process symbols equal to each other in the arrangement position in the first direction out of the plurality of process symbols,
wherein the execution order determination unit is further configured to determine an execution order of the at least two process symbols specified by the process symbol position specification unit based on the arrangement positions of the at least two process symbols in the second direction intersecting the first direction.

11. The operation command generation device according to claim 10,
wherein the protocol chart further comprises a consecutive process symbol arranged so as to be associated with a plurality of process symbols,
wherein the operation command generation device further comprises a consecutive process setting unit configured to set consecutive execution of processes represented by the plurality of process symbols, and
wherein the process symbol conversion unit is further configured to convert, based on the setting by the consecutive process setting unit, the plurality of process symbols into jobs to be consecutively executed for a single container.

12. The operation command generation device according to claim 1,
wherein the protocol chart further comprises a transfer symbol representing a transfer process of transferring the process subject from a first container to a second container, and
wherein the operation command generation device further comprises a transfer symbol conversion unit configured to convert the transfer symbol into a job of transferring the process subject from the first container to the second container.

13. The operation command generation device according to claim 12, further comprising a transfer rule setting unit configured to set a first transfer rule when a number of the first containers and a number of the second containers are equal to each other,
wherein the transfer symbol conversion unit is further configured to convert, based on the first transfer rule, the transfer symbol into a job of repeating a process of transferring the process subject from the first container to the second container in a one-to-one manner as many times as the number of the first containers.

14. The operation command generation device according to claim 12, further comprising a transfer rule setting unit configured to set a second transfer rule when a number of the first containers is at least two and the number of the second containers is one,
wherein the transfer symbol conversion unit is further configured to convert, based on the second transfer rule, the transfer symbol into a job of repeating a process of transferring the process subject from the first container to the second container for all the first containers.

15. The operation command generation device according to claim 12, further comprising a transfer rule setting unit configured to set a third transfer rule when a number of the first containers is one and a number of the second containers is at least two,
   wherein the transfer symbol conversion unit is further configured to convert, based on the third transfer rule, the transfer symbol into a job of repeating a process of transferring the process subject from the first container to the second container for all the second containers.

16. The operation command generation device according to claim 12, further comprising a transfer rule setting unit configured to set a fourth transfer rule when a number of the first containers is at least two and a number of the second containers is at least two,
   wherein the transfer symbol conversion unit is further configured to convert, based on the fourth transfer rule, the transfer symbol into a job of repeating a process of transferring the process subject from the first container to an intermediate container for all the first containers, and then repeating a process of transferring the process subject from the intermediate container to the second container for all the second containers.

17. The operation command generation device according to claim 12, further comprising a transfer rule setting unit configured to set a fifth transfer rule when a number of the first containers is at least two, a number of the second containers is at least two, and the number of the second containers is n times as many as the number of the first containers, where n is an integer,
   wherein the transfer symbol conversion unit is further configured to convert, based on the fifth transfer rule, the transfer symbol into a job of repeating a process of transferring the process subject from a single first container to n second containers for all the first containers and all the second containers.

18. The operation command generation device according to claim 12, further comprising a transfer rule setting unit configured to set a sixth transfer rule when a number of the first containers is at least two, a number of the second containers is at least two, and the number of the first containers is n times as many as the number of the second containers, where n is an integer,
   wherein the transfer symbol conversion unit is further configured to convert, based on the sixth transfer rule, the transfer symbol into a job of repeating a process of transferring the process subject from n first containers to a single second container for all the first containers and all the second containers.

19. The operation command generation device according to claim 12, further comprising a transfer rule setting unit configured to set a seventh transfer rule when a number of the first containers is at least two and a number of the second containers is at least two,
   wherein the transfer symbol conversion unit is further configured to convert, based on the seventh transfer rule, the transfer symbol into a job of repeating a process of transferring the process subject from a single first container to all the second containers for all the first containers.

20. An operation command generation method, comprising:
   determining, based on respective arrangement positions of a plurality of process symbols each representing a process for a process subject on a protocol chart comprising the plurality of process symbols, an execution order of the plurality of process symbols; and
   respectively converting the plurality of process symbols to jobs for a process system comprising at least a robot so that processes represented by the plurality of process symbols are executed in the execution order determined in the determining of the execution order,
   wherein the protocol chart further comprises an initial symbol with which at least one process symbol is associated, the initial symbol representing a container for the process subject,
   wherein some of the process symbols are arranged along a first direction from the initial symbol,
   wherein another initial symbol is arranged being separate from the initial symbol in a second direction intersecting the first direction, and the former initial symbol and the latter initial symbol represent different containers, and
   wherein the execution order of the processes represented by the process symbols arranged at equal position in the first direction is determined according to their position in the second direction.

21. A process system, comprising:
   the operation command generation device of claim 1;
   a robot controller configured to control a control subject based on an operation command generated by the operation command generation device; and
   a robot configured to carry out a process on a process subject, the robot being controlled by the robot controller.

* * * * *